United States Patent [19]
Goli et al.

[11] Patent Number: 5,863,898
[45] Date of Patent: Jan. 26, 1999

[54] HUMAN LIM PROTEINS

[75] Inventors: Surya K. Goli, Sunnyvale; Jennifer L. Hillman, San Jose; Olga Bandman, Mountain View, all of Calif.

[73] Assignee: Incyte Pharmaceuticals, Inc., Palo Alto, Calif.

[21] Appl. No.: 739,485

[22] Filed: Oct. 28, 1996

[51] Int. Cl.$^6$ .................................................. C07K 14/00
[52] U.S. Cl. ............................................ 514/12; 530/350
[58] Field of Search ................................ 514/12; 530/350

[56] References Cited

PUBLICATIONS

Dong et al, DNA and Cell Biology vol. 16 No. 6 671–678, 1997.
Arber, S., et al., "Muscle LIM Protein, a Novel Essential Regulator of Myogenesis, Promotes Myogenic Differentiation" *Cell,* 79:221–231 (1994).
Boehm, T., et al., "The mechanism of chromosomal translocation t(11;14) involving the T–cell receptor Cδlocus on human chromosome 14q11 and a transcribed region of chromosome 11p15" *EMBO J.,* 7:385–384 (1988).
Fisch, P., et al., "T–cell acute lymphoblastic lymphoma induced in transgenic mice by the *RBTN1* and *RBTN2* LIM–domain genes" *Oncogene,* 7:2389–2397 (1992).
Freyd, G., et al., "Novel cysteine–rich motif and homeodomain in the product of the *Caenorhabditis elegans* cell lineage gene *lin–II*" *Nature,* 44:876–879 (1990).
Jain, M.K., et al., "Molecular Cloning and Characterization of SmLIM, Developmentally Regulated LIM Protein Preferentially Expressed in Aortic Smooth Muscle Cells" *J. Biol. Chem.,* 271:10194–10199 (1996).
Karlsson, O., et al., "Insulin gene enhancer binding protein ISI–1 is a member of a novel class of proteins containing both a homeo–and a Cys–His domain" *Nature,* 344:879–882 (1990).
Kiess, M., et al., "Expression of ril, a novel LIM domain gene, is down–regulated in HRAS–transformed cells and restored in phenotypic revertants" *Oncogene,* 10:61–68 (1995).
Liebhaber, S., et al., "Characterization of a human cDNA encoding a widely expressed and highly conserved cysteine–rich protein with an unusual zinc–finger motif" *Nuc. Acids Res.,* 18:3871–3879 (1990).
McGuire, E.A., et al., "Thymic Overexpression of Ttg–1 in Transgenic Mice Results in T–Cell Acute Lymphoblapric Leukemia/Lymphoma" *Mol. and Cell. Biol.,* 12:4186–4196 (1992).
Sanchez–Garcia, I., et al., "The LIM domain: a new structural motif found in zinc–finger–like proteins" *TIG,* 10:315–320 (1994).
Schmeichel, K.L. et al., "The LIM Domain is a Modular Protein–Binding Interface" *Cell,* 79:211–219 (1994).
Wang, H., et al., "Cloning of a rat cDNA encoding a novel LIM domain protein with high homology to rat RIL" *Gene,* 165:267–271 (1995).
Wang, X., et al., "Human Cysteine–rich Protein" *J. Biol. Chem.,* 267:9176–9184 (1992).
Warren, A.J., et al., "The Oncogenic Cysteine–Rich LIM Domain Protein Rbtn2 is Essential for Erythroid Development" *Cell,* 78:45–57 (1994).
Way, J.C., et al., "mec–3, a Homebox–Containing Gene That Specifies Differentiation of the Touch Receptor Neurons in C. elegans" *Cell,* 54:5–16 (1988).
Weiskirchen, R. et al., (Accession No. U57646) EMBL Database, EMBL Database, Geneva, Switzerland May 1996.

*Primary Examiner*—Shela Huff
*Assistant Examiner*—Julie E. Reeves
*Attorney, Agent, or Firm*—Lucy J. Billings; Sheela Mohan-Peterson; Incyte Pharmaceuticals, Inc.

[57] ABSTRACT

The present invention provides three human LIM proteins (designated individually as HLIM-1, HLIM-2, and HLIM-3, and collectively as HLIM) and polynucleotides which identify and encode HLIM. The invention also provides genetically engineered expression vectors and host cells comprising the nucleic acid sequences encoding HLIM and a method for producing HLIM. The invention also provides for use of HLIM and agonists, antibodies, or antagonists specifically binding HLIM, in the prevention and treatment of diseases associated with expression of HLIM. Additionally, the invention provides for the use of antisense molecules to polynucleotides encoding HLIM for the treatment of diseases associated with the expression of HLIM. The invention also provides diagnostic assays which utilize the polynucleotide, or fragments or the complement thereof, and antibodies specifically binding HLIM.

2 Claims, 29 Drawing Sheets

```
                                                                    45                      54
5' CT GGA CCC TCC CTC CAG CCC AGC CTC GCT AGC TCC GCC TGC GGT ACG TGC TCC 63              72              81              90              99             108
CGC CTC CGA CTC AAA ATG CCT GTC TGG GGA GGT GGA AAC AAG TGT GGG GCC TGT
                     M   P   V   W   G   G   N   K   C   G   A   C 117             126             135             144             153             162
GGG AGG ACC GTG TAC CAC GCA GAA GAG GTG CAG TGT GAT GGC AGG AGC TTC CAC
 G   R   T   V   Y   H   A   E   E   V   Q   C   D   G   R   S   F   H 171             180             189             198             207             216
CGC TGC TGC TTT CTC TGC ATG GTT TGC AGG AAA AAT TTA GAT AGC ACA ACA GTG
 R   C   C   F   L   C   M   V   C   R   K   N   L   D   S   T   T   V 225             234             243             252             261             270
GCA ATT CAC GAT GAA GAG ATC TAC AAA TCC TGC TAC GGA AAG AAG TAT GGG
 A   I   H   D   E   E   I   Y   K   S   C   Y   G   K   K   Y   G 279             288             297             306             315             324
CCA AAA GGC TAC GGT TAT GGC CAG GCT GGC ACG CTT AAM ATG GAC CGT GGC
 P   K   G   Y   G   Y   G   Q   A   G   T   L   X   M   D   R   G 333             342             351             360             369             378
GAG AGG CTT GGC ATC AAA CCA GAG AGT GTT CAG CCT CAC AGG CCT ACA ACA AAT
 E   R   L   G   I   K   P   E   S   V   Q   P   H   R   P   T   T   N
```

FIGURE 1A

```
              387        396        405        414        423        432
CCA AAC AHT TCT AAA TTT GCT CAG AAA TAT GGA GGT GCT GAG AAG TGT TCC AGA
 P   N   X   S   K   F   A   Q   K   Y   G   G   A   E   K   C   S   R 441        450        459        468        477        486
TGT GGG GAT TCT GTA TAT GCT GCC GAG AAG ATA ATT GGA GCT GGA AAG CCC TGG
 C   G   D   S   V   Y   A   A   E   K   I   I   G   A   G   K   P   W 495        504        513        522        531        540
CAC AAA AAC TGT TTC CGA TGT GCA AAG TGT GGG AAG AGT CTT GAA TCA ACA ACT
 H   K   N   C   F   R   C   A   K   C   G   K   S   L   E   S   T   T 549        558        567        576        585        594
CTG ACT GAA AAA GAA GGT GAG ATT TAC TGC AAA GGA TGT TAT GCT AAA AAC TTC
 L   T   E   K   E   G   E   I   Y   C   K   G   C   Y   A   K   N   F 603        612        621        630        639        648
GGG CCC AAG GGC TTT GGT TTT GGG CAA GGA GCT GGG GCC TTG GTC CAC TCT GAG
 G   P   K   G   F   G   F   G   Q   G   A   G   A   L   V   H   S   E 657        666        675        684        693        702
TGA GGC CAC CAT CAC CCA CCA CAC CCT GCC CAC TCC TGC GCT TTT CAT CGC CAT 711        720        729        738        747        756
TCC ATT CCC AGC AGC TTT GGA GAC CTC CAG GAT TAT TTC TCT GTC AGC CCT GCC 765        774        783        792
ACA TAT CAC TAA TGA CTT GAA CTT GGG CAT CTG GCT CCC TTT 3'

FIGURE 1B
```

```
                                                                    45              54
5' GGC CCN NGC CGC GCC GCT NTN TCT CCN ACA NGC CGG GGG TGC CCT GCA AGC
      9          18              27          36

99             108
   TGT TCC GCG CGT CCT GCC CGT CTG TCC CCG CGG GTC GCC CGC CAC AGC CGC
     63          72              81          90

153             162
   GCC ATG ACC ACC CAG CAG ATA GAC CTC CAG GGC CCG TGG GGC TTC CGC
        M   T   T   Q   Q   I   D   L   Q   G   P   W   G   F   R
    117         126             135         144

207             216
   CTC GTG GGC AAG GAC TTC GAG CCT CAG CCT CTC GCC ATT TCC CGG GTC ACT CCT
    L   V   G   K   D   F   E   Q   P   L   A   I   S   R   V   T   P
    171         180             189         198

261             270
   GGA AGC AAG GCG GCT CTA GCT AAT TTA TGT ATT GGA GAT GTA ATC ACA GCC ATT
    G   S   K   A   A   L   A   N   L   C   I   G   D   V   I   T   A   I
    225         234             243         252

315             324
   GAT GGG GAA AAT ACT AGC AAT ATG ACA CAC TTG GAA GCT CAG AAC AGA ATC AAA
    D   G   E   N   T   S   N   M   T   H   L   E   A   Q   N   R   I   K
    279         288             297         306

369             378
   GGC TGC ACA GAC AAC TTG ACT CTC ACT GTA GCC AGA TCT GAA CAT AAA GTC TGG
    G   C   T   D   N   L   T   L   T   V   A   R   S   E   H   K   V   W
    333         342             351         360
```

FIGURE 2A

```
387             396             405             414             423             432
TCT CCT CTG GTG ACG GAG GAA GGG AAG CGT CAT CCA TAC AAG ATG AAT TTA GCC
 S   P   L   V   T   E   E   G   K   R   H   P   Y   K   M   N   L   A 441             450             459             468             477             486
TCT GAA CCC CAG GAG GTC CTG CAC ATA GGA AGC GCC CAC AAC CGA AGT GCC ATG
 S   E   P   Q   E   V   L   H   I   G   S   A   H   N   R   S   A   M 495             504             513             522             531             540
CCC TTT ACC GCC TCG CCT GCC TCC AGC ACT ACT GCC AGG GTC ATC ACA AAC CAG
 P   F   T   A   S   P   A   S   S   T   T   A   R   V   I   T   N   Q 549             558             567             576             585             594
TAC AAC CCA GCT GGC CTC TAC TCT TCT GAA AAT ATC TCC AAC TTC AAC AAT
 Y   N   P   A   G   L   Y   S   S   E   N   I   S   N   F   N   N 603             612             621             630             639             648
GCC CTG GAG TCA AAG ACT GCT GCC AGC AGC GTG GAG GCG AAC AGC AGA CCC TTA
 A   L   E   S   K   T   A   A   S   S   V   E   A   N   S   R   P   L 657             666             675             684             693             702
GAC CAT GCT CAG CCT CCA AGC AGC CTT GTC ATC GAC AAA GAA TCT GAA GTT TAC
 D   H   A   Q   P   P   S   S   L   V   I   D   K   E   S   E   V   Y 711             720             729             738             747             756
AAG ATG CTT CAG GAG AAA CAG GAG TTG AAT GAG CCC CCG AAA CAG TCC ACG TCT
 K   M   L   Q   E   K   Q   E   L   N   E   P   P   K   Q   S   T   S
```

FIGURE 2B

```
765                774              783              792              801              810
TTC TTG GTT TTG CAG GAA ATC CTG GAG TCT GAA GAA AAA GGG GAT CCC AAC AAG
 F   L   V   L   Q   E   I   L   E   S   E   E   K   G   D   P   N   K 819                828              837              846              855              864
CCC TCA GGA TTC AGA AGT GTT AAA GCT CCT GTC ACT AAA GTG GCT GCG TCG ATT
 P   S   G   F   R   S   V   K   A   P   V   T   K   V   A   A   S   I 873                882              891              900              909              918
GGA AAT GCT CAG AAG TTG CCT ATG TGT GAC AAA TGT GGC ACT GGG ATT GTT GGT
 G   N   A   Q   K   L   P   M   C   D   K   C   G   T   G   I   V   G 927                936              945              954              963              972
GTG TTT GTG AAG CTG CGG GAC CGT CAC CGC CAC CCT GAG TGT TAT GTG TGC ACT
 V   F   V   K   L   R   D   R   H   R   H   P   E   C   Y   V   C   T 981                990              999              1008             1017             1026
GAC TGT GGC ACC AAC CTG AAA CAG GGC CAT TTC TTT GTG GAG GAT CAA ATC
 D   C   G   T   N   L   K   Q   G   H   F   F   V   E   D   Q   I 1035               1044             1053             1062             1071             1080
TAC TGT GAG AAG CAT GCC CGG GAG GTC ACA CCA CCT GAG GGT TAT GAA GTG
 Y   C   E   K   H   A   R   E   V   T   P   P   E   G   Y   E   V 1089               1098             1107             1116             1125             1134
GTC ACT GTG TTC CCC AAG TGA GCC AGC AGA TCY GAC CAC TGT TCT CCA GCA GGC
 V   T   V   F   P   K
```

FIGURE 2C

```
       1143        1152        1161        1170             1179         1188
CTC TGC TGC AGC TTT TTC TCT CAG TGT TCT GGC CCT CTC CTC TCT TGA AAG TTC
  1197        1206        1215        1224
TCT GCC TAC TTT GGT TTT CCC TCT GCT TGT AAA ACA T 3'
```

FIGURE 2D

```
5' 
    C GGC AGC GGC TCG AGG GCG CGG AGT GGC TGC CCT GCG CGG GGA CAC TCA
                9      18       27       36       45       54

GAG CCC GGT GGG CGG GAG GAA GGC ATG CCC CAG ACG GTG ATC CTC CCG GGC
 63       72       81       90       99                  108
                           M   P   Q   T   V   I   L   P   G

CCT GCG CCC TGG GGC TTC AGG CTC TCA GGG GGC ATA GAC TTC AAC CAG CCT TTG
117      126      135      144      153                 162
 P   A   P   W   G   F   R   L   S   G   G   I   D   F   N   Q   P   L

GTC ATC ACC AGG ATT ACA CCA GGA AGC AAG GCG GCA GCT GCC AAC CTG TGT CCT
171      180      189      198      207                 216
 V   I   T   R   I   T   P   G   S   K   A   A   A   A   N   L   C   P

GGA GAT GTC ATC CTG GCT ATT GAC GGC TTT GGG ACA GAG TCC ATG ACT CAT GCT
225      234      243      252      261                 270
 G   D   V   I   L   A   I   D   G   F   G   T   E   S   M   T   H   A

GAT GCG CAG GAC AGG ATT AAA GCA GCA GCT CAC CAG CTG TGT CTC AAA ATT GAC
279      288      297      306      315                 324
 D   A   Q   D   R   I   K   A   A   A   H   Q   L   C   L   K   I   D

AGG GGA GAA ACT CAC TTA TGG TCT CCA CAA GTA TCT GAA GAT GGG AAA GCC CAT
333      342      351      360      369                 378
 R   G   E   T   H   L   W   S   P   Q   V   S   E   D   G   K   A   H
```

FIGURE 3A

```
        387            396       405       414       423       432
CCT TTC AAA ATC AAC TTA GAA TCA GAA CCA CAG GAA TTC AAA CCC ATT GGT ACC
 P   F   K   I   N   L   E   S   E   P   Q   E   F   K   P   I   G   T
        441            450       459       468       477       486
GCG CAC AAC AGA AGG GCC CAG CCT TTT GTT GCA GCT GCA AAC ATT GAT GAC AAA
 A   H   N   R   R   A   Q   P   F   V   A   A   A   N   I   D   D   K
        495            504       513       522       531       540
AGA CAG GTA GTG AGC GCT TCC TAT AAC TCG CCA ATT GGG CTC TAT TCA ACT AGC
 R   Q   V   V   S   A   S   Y   N   S   P   I   G   L   Y   S   T   S
        549            558       567       576       585       594
AAT ATA CAA GAT GCG CTT CAC GGA CAG CTG CGG GGT CTC ATT CCT AGC TCA CCT
 N   I   Q   D   A   L   H   G   Q   L   R   G   L   I   P   S   S   P
        603            612       621       630       639       648
CAA AAC GAG CCC ACA GCC TCG GTG CCC CCC GAG TCG GAC GTG TAC CGG ATG CTC
 Q   N   E   P   T   A   S   V   P   P   E   S   D   V   Y   R   M   L
        657            666       675       684       693       702
CAC GAC AAT CGG AAT GAG CCC ACA CAG CCT CGC CAG TCG GGC TCC TTC AGA GTG
 H   D   N   R   N   E   P   T   Q   P   R   Q   S   G   S   F   R   V
        711            720       729       738       747       756
CTC CAG GGA ATG GTG GAC GAT GGG TTT GAT GAC CGT CCG GCT CCG GGA ACG CGG AGT
 L   Q   G   M   V   D   D   G   F   D   D   R   P   A   P   G   T   R   S
```

FIGURE 3B

```
                                          765                    774                    783                    792                    801                    810
                                   GTG AGA GCT CCG GTG ACG AAA GTC CAT GGC GGT TCA GGC GGG GCA CAG AGG ATG
                                    V   R   A   P   V   T   K   V   H   G   G   S   G   G   A   Q   R   M 819                    828                    837                    846                    855                    864
                                   CCG GTC TGT GAC AAA TGT GGG AGT ATA GTT GGT GCT GTG AAG GCG CGG
                                    P   V   C   D   K   C   G   S   I   V   G   A   V   K   A   R 873                    882                    891                    900                    909                    918
                                   GAT AAG TAC CGG CAC CCT GAG TGC TTC GTG TGT GCC GAC TGC AAC CTC AAC CTC
                                    D   K   Y   R   H   P   E   C   F   V   C   A   D   C   N   L   N   L 927                    936                    945                    954                    963                    972
                                   AAG CAA AAG GGC TAC TTC TTC ATA GAA GGG GAG CTG TAC TGC GAA ACC CAC GCA
                                    K   Q   K   G   Y   F   F   I   E   G   E   L   Y   C   E   T   H   A 981                    990                    999                    1008                   1017                   1026
                                   AGA GCC CGC ACA AAG CCC CCA GAG CCC CCA GAG GGC TAT GAC GTC ACT CTG TAT CCC AAA
                                    R   A   R   T   K   P   P   E   P   P   E   G   Y   D   V   T   L   Y   P   K 1035                   1044                   1053                   1062                   1071                   1080
                                   GCT TAA GTC TCT GCA GGC GTG GCA CGC ACG CAC GCA CCC ACC CAC GCG CCA CTT
                                    A   *

1089                   1098                   1107                   1116                   1125                   1134
                                   ACA CGA GAA GAC ATT CAT GGC TTT GGG CAG AAG GAT TGT GCA GAT TGT CAA CTC
```

FIGURE 3C

```
              1143          1152          1161          1170          1179          1188
CAA ATC TAA AGT CAA GGC TTT AGA CCT TTA TCC TAT TGT TTA TTG AGG AAA AGG 1197          1206          1215          1224          1233          1242
AAT GGG AGG CAA ATG CCT GCT ATG TGA AAA AAA CAT ACA CTT AGC TAT GTT TTG 1251          1260          1269          1278          1287          1296
CAA CTC TTT TTG GGG CTA GCA ATA ATG ATA TTT AAA GCA ATA ATT TTT TGT ATG 1305          1314          1323          1332
TCA TAC TCC ACA ATT TAC ATG TAT ATT ACA GCC ATC AAA CAC   3'
```

FIGURE 3D

```
  1 M P V W G G G N K C G A C G R T V Y H A E E V Q C D G R S F H R C C F L C M V C    HLIM-1
  1 M P N W G G G K K C G V C Q K T V Y F A E E V Q C E G N S F H K S C F L C M V C    GI 118161
  1 M P N W G G G A K C G A C E K T V Y H A E E I Q C N G R S F H K T C F H C M A C    GI 1234841
  1 M P V W G G G N K C G A C G R T V Y H A E E V Q C D G R T F H R C C F L C M V C    GI 1314351

41 R K N L D S T T V A I H D E E I Y C K S C Y G K K Y G P K G Y G Q G A G T L        HLIM-1
 41 K K N L D S T T V A V H G E E I Y C K S C Y G K K Y G P K G Y G Q G A G T L        GI 118161
 41 R K A L D S T T V A A H E S E I Y C K V C Y G R R Y G P K G I G Q G A G C L        GI 1234841
 41 R K N L D S T T V A I H D E E I Y C K S C Y G K K Y G P K G Y G Q G A G T L        GI 1314351

81 X M D R G E R L G I K - P E S V Q P H R P T T N P N X S K F A Q K Y G G A E K C    HLIM-1
 81 S T D K G E S L G I K - H E E A P G H R P T T N P N A S K F A Q K I G G S E R C    GI 118161
 81 S T D T G E H L G L Q F Q Q S P K P A R S V T T S N P S K F T A K F G E S E K C    GI 1234841
 81 N M D R G E R L G I K - P E S A Q P H R P T T N P N T S K F A Q K Y G G A E K C    GI 1314351

120 S R C G D S V Y A A A E K I I G A G K P W H K N C F R C A K C G K S L E S T T L T    HLIM-1
120 P R C S Q A V Y A A A E K V I G A G K S W H K A C F R C A K C G K G L E S T T L A    GI 118161
121 P R C G K S V Y A A A E K V M G G G K P W H K T C F R C A I C C G K S T N V T        GI 1234841
120 S R C G D S V Y A A A E K I I G A G K P W H K N C F R C A K C G K S L E S T T L T    GI 1314351

160 E K E G E I Y C K G C Y A K N F G P K G F G F G Q G Q G A G A L V H S E              HLIM-1
160 D K D G E I Y C K G C Y A K N F G P K G F G F G Q G Q G A G A L V H S E              GI 118161
161 D K D G E L Y C K V C Y A K N F G P T G I G F G L T Q Q V E K K E                    GI 1234841
160 E K E G E I Y C K G C Y A K N F G P K G F G Y G Q G A G A L V H A Q                  GI 1314351
```

```
  1  M T T Q Q I D L Q G P G P W G F R L V G G K D F E Q P L A I S R V T P G S K A A   HLIM-2
  1  M T T Q Q I V L Q G P G P W G F R L V G G K D F E Q P L A I S R V T P G S K A A   GI 1020151
  1  M T - H A V T L R G P S P W G F R L V G G R D F S A P L T I S R V H A G S K A A   GI 887580

41  L A N L C I G D V I T A I D G E N T S N M T H L E A Q N R I K G C T D N L T L T   HLIM-2
 41  I A N L C I G D L I T A I D G E D T S S M T H L E A Q N K I K G C V D N M T L T   GI 1020151
 40  L A A L C P G D S I Q A I N G E S T E L M T H L E A Q N R I K G C H D H L T L S   GI 887580

81  V A R S E H K V W S P L V T E E G K R H P Y K M N L A S E P Q E V L H I G S A H   HLIM-2
 81  V S R S E Q K I W S P L V T E E G K R H P Y K M N L A S E P Q E V L H I G S A H   GI 1020151
 80  V S R P E N K N W P S - - S P N D K A Q A H R I H I D P E A Q D - - - G S P A     GI 887580

121  N R S A M P F T A S P A S S T T A R V I T N Q Y N N P A G L Y S S E N I S N F N   HLIM-2
121  N R S A M P F T A S P A S S T T A R V I T N Q Y N S P T G L Y S S E N I S N F N   GI 1020151
114  T S R R S S I S G I S L E D N R S - G L G S P Y G Q P P R L P V P H N G S N E     GI 887580

161  N A L E S K T A A S G V E A N S R P L D H A Q P P S S L V I D K E - - - - - - -   HLIM-2
159  N A V E S K T S A S G E E A N S R P S A Q P H P S G G L I I D K E - - - - - S -   GI 1020151
153  V T L P S Q M S A - - - L H V S P P P S A D T P R I L P R N R D C R V D L G S     GI 887580

195  E V Y K M L Q E K Q E L N E P - P K Q S T S F L V L Q E I L E S E E K G D P N K   HLIM-2
193  E V Y K M L Q E K Q E L N E P - P K Q S T S F L V L Q E I L E S D G K G D P N K   GI 1020151
189  E V Y R M L R E P A A S E P K Q S G S F R Y L Q G M L E A G E G G D R P G         GI 887580
```

```
234  P S G F R S V K A P V T K V A A S I G N A Q K L P M C D K C G T G I V G V F V K   HLIM-2
232  P S G F R S V K A P V T K V A A S V G N A Q K L P I C D K C G T G I V G V F V K   GI 1020151
229  S G G S R N L K P A A S K L G A P L S G L Q G L P E C T R C G H G I V G T I V K   GI 887580

274  L R D R H R H P E C Y V C T D C G T N L K Q K G H F F V E D Q I Y C E K H A R E   HLIM-2
272  L R D H H P H P E C Y V C T D C G I N L K Q K G H F F V G D Q I Y C E K H A R E   GI 1020151
269  A R D K L Y H P E C F M C S D C G L N L K Q R G Y F F L D E R L Y C E N H A K A   GI 887580

314  R V T P P E G Y E V V T V F P K                                                   HLIM-2
312  R V T P P E G Y D V V T V F P K                                                   GI 1020151
309  R V K P P E G Y D V V A V Y P N A K V E L V                                       GI 887580
```

FIGURE 5B

```
  1  MP-QTVILPGPAPWGFRLSGGIDFNQPLVITRITPGSKAA      HLIM-3
  1  MTQQIVLQGPGPWGFRLVGGKDFEQPLAISRVTPGSKAA       GI 1020151
  1  M--THAVTLRGPSPWGFRLVGGRDFSAPLTHISRVHAGSKAA    GI 887580

40  AANLCPGDVILAIDGFGTESMTHADAQDRIKAAAHQLCLK      HLIM-3
 41  IANLCIIGDLITAIDGEDTSSMTHLEAQNKIKGCVDNMTLT     GI 1020151
 40  LAALCPGDSIQAINGESTELMTHLEAQNRIKGCHDHLTLS      GI 887580

80  IDRGETHLWSPQVSEDGKAHPFKINLESEPQEFKPIGTAH      HLIM-3
 81  VSRSEQKIWSPLVTEEGKRHPYKMNLASEPQEVLHIGSAH      GI 1020151
 80  VSRPENKNWPS--SPNDKAQAHRIHIDPEAQDGSPATSRR      GI 887580

120  NRRAQPFVAAANIDDKRQVVSASYNSPIGLYSTSNI---Q      HLIM-3
121  NRSAMPFTASPAPGTR--VITNQYNSPTGLYSSENISNFN      GI 1020151
118  SS---ISGISLEDNRSGLGSPYGQPPRLPVPHNGSSNE        GI 887580

157  DALHGQLRGL----IPSSPQNEPTAS--VPPE-----S        HLIM-3
159  NAVESKTSASGEEANSRPSAQPHPSGGLIIDKE-----S       GI 1020151
153  VTLPSQMSAL------HVSPPPSADTPRILPRNRDCRVDLGS    GI 887580

184  DVYRMLHDNRN-EPTQPRQSGSFRVLQGMVDD--GFDDR       HLIM-3
193  EVYKMLQEKQE-LNEPPKQSTSFLVLQEILESDGKGDPNK      GI 1020151
189  EVYRMLREPAASEPKQSGSFRYLQGMLEAGEGGDRPG         GI 887580
```

FIGURE 6A

```
220 PAGTRSVRAPVTKVHGGSGGAQRMPVCDKCGSGIVGAVVK   HLIM-3
232 PSGFRSVKAPVTKVAASVGNAQKLPICDKCGTGIVGVFVK    GI 1020151
229 SGGSRNLKPAASKLGAPLSGLQGLPECTRCGHGIVGTIVK    GI 887580

260 ARDKYRHPECFVCADCNLNLKQKGYFFIEGELYCETHARA    HLIM-3
272 LRDHHPHPECYVCTDCGINLKQKGHFFVGDQIYCEKHARE    GI 1020151
269 ARDKLYHPECFMCSDCGLNLKQRGYFFLDERLYCENHAKA    GI 887580

300 RTKPPEGYDTVTLYPKA                           HLIM-3
312 RVTPPEGYDVVTVFPK                            GI 1020151
309 RVKPPEGYDVVAVYPNAKVELV                      GI 887580
```

FIGURE 6B

| Library | Lib Description | Abun | Pct Abun |
|---|---|---|---|
| HEARNOT01 | heart, 56 M | 4 | 0.2851 |
| BLADNOT03 | bladder, 80 F, match to BLADTUT02 | 4 | 0.1084 |
| BRAINOT09 | brain, fetal M | 2 | 0.0524 |
| PROSNOT14 | prostate, 60 M, match to PROSTUT08 | 2 | 0.0512 |
| PLACNOM03 | placenta, fetal, NORM, WM | 1 | 0.0363 |
| PROSNOT06 | prostate, 57 M, match to PROSTUT04 | 3 | 0.0343 |
| SPLNFEM01 | spleen, fetal, WM | 1 | 0.0332 |
| FIBRSEM01 | fibroblasts, senescent, NORM, WM | 1 | 0.0310 |
| BRAITUT03 | brain tumor, astrocytoma, 17 F | 2 | 0.0308 |
| BLADTUT02 | bladder tumor, 80 F, match to BLADNOT03 | 1 | 0.0305 |
| LUNGFEM01 | lung, fetal, NORM, WM | 2 | 0.0296 |
| BRAITUT12 | brain tumor, astrocytoma, 40 F, match to BRAINOT14 | 1 | 0.0272 |
| URETTUT01 | ureter tumor, 69 M | 1 | 0.0262 |
| BLADTUT04 | bladder tumor, 60 M, match to BLADNOT05 | 2 | 0.0253 |
| LIVRNOT01 | liver, 49 M | 1 | 0.0198 |
| THYMNOT02 | thymus, 3 M | 1 | 0.0194 |
| BRAINOT03 | brain, 26 M | 1 | 0.0185 |
| HNT2NOT01 | hNT2 cell line, teratocarcinoma, control | 1 | 0.0173 |
| BRAITUT02 | brain tumor, metastasis, 58 M | 1 | 0.0170 |
| SINTBST01 | small intestine, ileum, Crohn's, 18 F | 1 | 0.0168 |
| UTRSNOT02 | uterus, 34 F | 1 | 0.0167 |
| BRSTNOT03 | breast, 54 F, match to BRSTTUT02 | 1 | 0.0147 |
| THYRNOT03 | thyroid tumor, adenoma, 28 F | 1 | 0.0138 |
| LATRTUT02 | heart tumor, myoma, 43 M | 1 | 0.0137 |
| CARDFEM01 | heart, fetal, NORM, WM | 1 | 0.0112 |

FIGURE 12

| Library | Lib Description | Abun | Pct Abun |
|---|---|---|---|
| OVARNON01 | ovary, 59 F, NORM | 5 | 0.7974 |
| BRSTNOT01 | breast, 56 F | 37 | 0.7129 |
| PLACNOT02 | placenta, fetal F | 30 | 0.5038 |
| SYNORAT01 | synovium, elbow, rheumatoid, 51 F | 9 | 0.4300 |
| LUNGNOM01 | lung, 72 M, WM | 15 | 0.4009 |
| UTRSNOT02 | uterus, 34 F | 24 | 0.3999 |
| MUSCNOT02 | muscle, psoas, 12 M | 10 | 0.3855 |
| SYNORAB01 | synovium, hip, rheumatoid, 68 F | 19 | 0.3710 |
| LUNGNOT02 | lung, 47 M | 15 | 0.3686 |
| RATRNOT01 | heart, right atrium, 51 F | 4 | 0.3497 |
| OVARNOT02 | ovary, 59 F | 11 | 0.3472 |
| SYNOOAT01 | synovium, knee, osteoarthritis, 82 F | 19 | 0.3417 |
| LUNGNOT01 | lung, 72 M | 10 | 0.3381 |
| PGANNON02 | paraganglionic tumor, benign paraganglioma, 46 M, NORM | 3 | 0.3209 |
| THYRNOT01 | thyroid, 64 F | 14 | 0.3207 |
| LATRNOT01 | heart, left atrium, 51 F | 12 | 0.3192 |
| KIDNNOT01 | kidney, 64 F | 2 | 0.3155 |
| UTRSNOT01 | uterus, 59 F | 8 | 0.3148 |
| SYNORAT05 | synovium, knee, rheumatoid, 62 F | 11 | 0.3147 |
| SKINBIT01 | skin, leg, erythema nodosum | 12 | 0.3071 |
| PANCNOT07 | pancreas, fetal M | 10 | 0.2866 |
| MYOMNOT01 | uterus, myometrium, 43 F | 7 | 0.2863 |
| LUNGNOT09 | lung, fetal M | 10 | 0.2858 |
| HEARNOT01 | heart, 56 M | 4 | 0.2851 |
| FIBRNOT01 | WI38 lung fibroblast cell line, fetal F | 6 | 0.2813 |

FIGURE 13A

| | | | |
|---|---|---|---|
| BLADNOT01 | bladder, 78 F | 8 | 0.2802 |
| PLACNOB01 | placenta, neonatal F | 11 | 0.2765 |
| BRSTNOT03 | breast, 54 F, match to BRSTTUT02 | 18 | 0.2643 |
| COLNNOT27 | large intestine, cecum, Crohn's, 31 M | 4 | 0.2505 |
| FIBRSEM01 | fibroblasts, senescent, NORM, WM | 8 | 0.2478 |
| LUNGAST01 | lung, asthma, 17 M | 25 | 0.2360 |
| MPHGNOT03 | macrophages (adher PBMNC), M/F | 18 | 0.2328 |
| PANCNOT08 | pancreas, 65 F, match to PANCTUT01 | 9 | 0.2285 |
| LUNGNOT12 | lung, 78 M | 8 | 0.2223 |
| OVARNOT07 | ovary, 28 F | 8 | 0.2152 |
| RATRNOT02 | heart, right atrium, 39 M | 9 | 0.2134 |
| ADRENOT01 | adrenal gland, 10-46 M/F | 2 | 0.2103 |
| LVENNOT02 | heart, left ventricle, 39 M | 1 | 0.2096 |
| CONNNOT01 | fat, mesentary, 71 M | 14 | 0.2083 |
| BRSTNOT05 | breast, 58 F, match to BRSTTUT03 | 13 | 0.2008 |
| CORNNOT01 | corneal fibroblasts, 76y | 2 | 0.1998 |
| UTRSNOT05 | uterus, 45 F | 7 | 0.1946 |
| BLADTUT07 | bladder, microfoci tumor, 58 M | 7 | 0.1943 |
| COLNNOT01 | colon, 75 M, match to COLNTUT02 | 9 | 0.1919 |
| SINTTUT01 | small intestine tumor, 42 M | 5 | 0.1908 |
| COLNCRT01 | colon, Crohn's, 40 M, match to COLNNOT05 | 4 | 0.1874 |
| BLADNOT06 | bladder, 66 M, match to BLADTUT05 | 7 | 0.1868 |
| BRSTNOM02 | breast, F, NORM, WM | 9 | 0.1858 |
| COLNFET02 | colon, fetal F | 13 | 0.1857 |
| STOMNOT02 | stomach, 52 M, match to STOMTUT01 | 6 | 0.1846 |
| BRSTNOT07 | breast, 43 F | 6 | 0.1843 |
| FIBRNOT02 | GD23A fibroblasts, control | 1 | 0.1838 |
| URETTUT01 | ureter tumor, 69 M | 7 | 0.1832 |
| LVENNOT01 | heart, left ventricle, 51 F | 4 | 0.1816 |

FIGURE 13B

| ID | Description | | Value |
|---|---|---|---|
| THP1PLB01 | THP-1 promonocyte cell line, treated PMA, LPS | 4 | 0.1809 |
| LUNGNOT03 | lung, 79 M, match to LUNGTUT02 | 9 | 0.1803 |
| BLADTUT04 | bladder tumor, 60 M, match to BLADNOT05 | 14 | 0.1773 |
| PROSTUT03 | prostate tumor, 67 M, match to PROSNOT05 | 5 | 0.1761 |
| SYNORAT04 | synovium, wrist, rheumatoid, 62 F | 10 | 0.1741 |
| SINTNOT02 | small intestine, 55 F | 5 | 0.1729 |
| BRSTNOT04 | breast, 62 F | 18 | 0.1728 |
| COLNNOT08 | colon, 60 M | 4 | 0.1703 |
| SYNORAT03 | synovium, wrist, rheumatoid, 56 F | 10 | 0.1696 |
| BRAINON01 | brain, 26 M, NORM | 4 | 0.1667 |
| FIBRNGT01 | GD23A fibroblasts, radiation 5 min | 1 | 0.1667 |
| MENTUNON3 | brain tumor, benign meningioma, 35 F, NORM | 1 | 0.1667 |
| CONNTUT01 | skull tumor, chondroid chordoma, 30 F | 6 | 0.1624 |
| BRAINOT11 | brain, right temporal, epilepsy, 5 M | 5 | 0.1611 |
| SCORNOT01 | spinal cord, 71 M | 8 | 0.1609 |
| PGANNOT03 | paraganglionic tumor, benign paraganglioma, 46 M | | |
| COLNNOT13 | colon, ascending, 28 M | 5 | 0.1555 |
| NGANNOT01 | ganglioneuroma, 9 M | 5 | 0.1553 |
| BRSTNOT09 | breast, 45 F, match to BRSTTUT08 | 10 | 0.1552 |
| HEARFET01 | heart, fetal M | 6 | 0.1529 |
| OVARNOM01 | ovary, 49 F, WM | 6 | 0.1524 |
| BRSTTUT03 | breast tumor, 58 F, match to BRSTNOT05 | 2 | 0.1504 |
| LUNGNOT04 | lung, 2 M | 15 | 0.1479 |
| | | 8 | 0.1464 |
| PROSNOT15 | prostate, 66 M, match to PROSTUT10 | 6 | 0.1448 |
| COLNNOT05 | colon, 40 M, match to COLNCRT01 | 5 | 0.1443 |
| LIVSFEM02 | liver/spleen, fetal M, NORM, WM | 54 | 0.1423 |
| SCORNON01 | spinal cord, 71 M, NORM | 1 | 0.1379 |
| OLFENOM01 | epithelium, olfactory, 35 F, WM | 1 | 0.1330 |

FIGURE 13C

| | | | |
|---|---|---|---|
| BSTMNON02 | brain stem, 72 M, NORM | 4 | 0.1275 |
| PROSNOT16 | prostate, 68 M | 5 | 0.1250 |
| BSTMNOT01 | brain stem, 72 M | 1 | 0.1214 |
| LUNGFEM01 | lung, fetal, NORM, WM | 8 | 0.1185 |
| COLNNOT09 | colon, 60 M | 3 | 0.1171 |
| PLACNOM01 | placenta, fetal M, WM | 2 | 0.1160 |
| COCHFEM01 | ear, cochlea, fetal, WM | 1 | 0.1157 |
| KIDNNOT05 | kidney, neonatal F | 7 | 0.1130 |
| UTRSNOT06 | uterus, myometrium, 50 F | 4 | 0.1129 |
| BRSTNOT02 | breast, 55 F, match to BRSTTUT01 | 10 | 0.1109 |
| LUNGNOT15 | lung, 69 M, match to LUNGTUT03 | 4 | 0.1106 |
| LUNGFET03 | lung, fetal F | 12 | 0.1096 |
| PLACNOM03 | placenta, fetal, NORM, WM | 3 | 0.1088 |
| BLADNOT03 | bladder, 80 F, match to BLADTUT02 | 4 | 0.1084 |
| BRAITUT01 | brain tumor, oligoastrocytoma, 50 F | 8 | 0.1076 |
| PROSTUT10 | prostate tumor, 66 M, match to PROSNOT15 | 4 | 0.1073 |
| SPLNFET01 | spleen, fetal | 3 | 0.1057 |
| BRAINOT10 | brain, cerebellum, Alzheimer's, 74 M | 3 | 0.1045 |
| SCORNON02 | spinal cord, 71 M, NORM | 3 | 0.1036 |
| LIVRBCT01 | liver, primary biliary cirrhosis | 1 | 0.1032 |
| BRSTTUT08 | breast tumor, 45 F, match to BRSTNOT09 | 4 | 0.1015 |
| BRAINOM01 | brain, infant F, NORM, WM | 22 | 0.0980 |
| LATRTUT02 | heart tumor, myoma, 43 M | 7 | 0.0962 |
| PGANNOT01 | paraganglionic tumor, benign paraganglioma, 46 M | 6 | 0.0960 |
| BRAINOT14 | brain, 40 F, match to BRAITUT12 | 3 | 0.0944 |
| PLACNOM02 | placenta, neonatal F, NORM, WM | 17 | 0.0944 |
| PANCDIT01 | pancreas, juvenile IDDM, 15 M | 2 | 0.0914 |
| BRAINOT12 | brain, right frontal, epilepsy, 5 M | 3 | 0.0910 |

FIGURE 13D

| | | | |
|---|---|---|---|
| RETNNOM01 | retina, 55 M, NORM, WM | 3 | 0.0908 |
| BRAINOM02 | brain, 55 M, NORM, WM | 2 | 0.0907 |
| CARDFEM01 | heart, fetal, NORM, WM | 8 | 0.0893 |
| MUSCNOT01 | muscle, skeletal | 2 | 0.0890 |
| TONGTUT01 | tongue tumor, carcinoma, 36 M | 3 | 0.0886 |
| COLNTUT06 | large intestine, cecal tumor, 45 F | 3 | 0.0880 |
| PROSNOT11 | prostate, 28 M | 3 | 0.0847 |
| PROSTUT12 | prostate tumor, 65 M, match to PROSNOT20 | 3 | 0.0838 |
| BLADNOT04 | bladder and seminal vesicle, 28 M | 3 | 0.0833 |
| COLNNOT22 | colon, 56 F | 3 | 0.0831 |
| THYRNOT03 | thyroid tumor, adenoma, 28 F | 6 | 0.0830 |
| PROSNOT19 | prostate, 59 M | 3 | 0.0815 |
| PENITUT01 | penis tumor, carcinoma, 64 M | 3 | 0.0800 |
| LUNGNOT10 | lung, fetal M | 3 | 0.0782 |
| LUNGNOT14 | lung, 47 M | 3 | 0.0778 |
| CERVNOT01 | cervix, 35 F | 4 | 0.0775 |
| PANCTUT01 | pancreatic tumor, 65 F, match to PANCNOT08 | 3 | 0.0773 |
| MELANOM01 | melanocytes, M, NORM, WM | 8 | 0.0769 |
| PROSNOT14 | prostate, 60 M, match to PROSTUT08 | 3 | 0.0767 |
| MENITUT03 | brain tumor, benign meningioma, 35 F | 3 | 0.0748 |
| BRAINOT03 | brain, 26 M | 4 | 0.0742 |
| GBLATUT01 | gall bladder tumor, 78 F | 3 | 0.0724 |
| HIPONOT01 | brain, hippocampus, 72 F | 3 | 0.0717 |
| MMLR1DT01 | macrophages (adher PBMNC), M/F, 24-hr MLR | 3 | 0.0708 |
| PROSNOT01 | prostate, 78 M | 2 | 0.0702 |
| PITUNOT03 | pituitary, 46 M | 2 | 0.0697 |
| PROSNOT06 | prostate, 57 M, match to PROSTUT04 | 6 | 0.0685 |
| ADRENOT03 | adrenal gland, 17 M | 2 | 0.0682 |
| LVENNOT03 | heart, left ventricle, 31 M | 2 | 0.0677 |

FIGURE 13E

| | | | |
|---|---|---|---|
| HIPONON01 | brain, hippocampus, 72 F, NORM | 2 | 0.0675 |
| COLNTUT02 | colon tumor, 75 M, match to COLNNOT01 | 3 | 0.0661 |
| SPLNNOT02 | spleen, 29 M | 3 | 0.0659 |
| OVARTUT01 | ovarian tumor, 43 F, match to OVARNOT03 | 2 | 0.0646 |
| COLNNOT16 | colon, sigmoid, 62 M, match to COLNTUT03 | 3 | 0.0624 |
| COLNNOT11 | colon, 60 M | 2 | 0.0617 |
| BLADTUT02 | bladder tumor, 80 F, match to BLADNOT03 | 2 | 0.0610 |
| THYRNOT02 | thyroid, hyperthyroidism, 16 F | 2 | 0.0607 |
| BRSTTUT02 | breast tumor, 54 F, match to BRSTNOT03 | 2 | 0.0597 |
| PROSTUT04 | prostate tumor, 57 M, match to PROSNOT06 | 5 | 0.0586 |
| COLNNOT19 | large intestine, cecum, 18 F | 2 | 0.0585 |
| PROSNON01 | prostate, 28 M, NORM | 2 | 0.0585 |
| THYMNOT02 | thymus, 3 M | 3 | 0.0582 |
| BEPINOT01 | bronchial epithelium, primary cell line, 54 M | 4 | 0.0577 |
| BRSTTUT01 | breast tumor, 55 F, match to BRSTNOT02 | 6 | 0.0567 |
| LUNGTUT02 | lung tumor, metastasis, 79 M, match to LUNGNOT03 | 3 | 0.0567 |
| TESTNOT03 | testis, 37 M | 1 | 0.0558 |
| BEPINON01 | bronchial epithelium, primary cell line, 54 M, NORM | 2 | 0.0547 |
| PTHYTUM01 | parathyroid tumor, adenoma, M/F, NORM, WM | 2 | 0.0535 |
| KIDNNOT09 | kidney, fetal M | 2 | 0.0534 |
| BLADNOT05 | bladder, 60 M, match to BLADTUT04 | 2 | 0.0528 |
| BRSTNOM01 | breast, F, NORM, WM | 2 | 0.0528 |
| DUODNOT02 | small intestine, duodenum, 8 F | 2 | 0.0525 |
| BRAINOT09 | brain, fetal M | 2 | 0.0524 |
| LIVRTUT01 | liver tumor, metastasis, 51 F | 2 | 0.0518 |
| COLNPOT01 | colon polyp, 40 F | 2 | 0.0513 |
| PROSNOT18 | prostate, hyperplasia, 58 M | 2 | 0.0513 |

FIGURE 13F

| | | | |
|---|---|---|---|
| SPLNNOT04 | spleen, 2 M | 4 | 0.0511 |
| BLADTUT06 | bladder tumor, carcinoma, 58 M | 1 | 0.0507 |
| OVARNOT03 | ovary, 43 F, match to OVARTUT01 | 3 | 0.0502 |
| U937NOT01 | U937 monocyte cell line, 37 M | 1 | 0.0497 |
| LUNGTUT03 | lung tumor, 69 M, match to LUNGNOT15 | 3 | 0.0478 |
| TESTNOT01 | testis, 37 M | 1 | 0.0478 |
| PITUNOT01 | pituitary, 16-70 M/F | 1 | 0.0472 |
| CORPNOT02 | brain, corpus callosum, Alzheimer's, 74 M | 3 | 0.0459 |
| NERVMSM01 | multiple sclerosis, 46 M, NORM, WM | 2 | 0.0449 |
| BMARNOR02 | bone marrow, 16-70 M/F, RP | 1 | 0.0442 |
| PANCNOT01 | pancreas, 29 M | 2 | 0.0428 |
| HUVENOB01 | HUVEC endothelial cell line, control | 1 | 0.0420 |
| EOSIHET02 | eosinophils, hypereosinophilia, 48 M | 4 | 0.0419 |
| THP1PLB02 | THP-1 promonocyte cell line, treated PMA, LPS | 1 | 0.0407 |
| PANCTUT02 | pancreatic tumor, carcinoma, 45 F | 2 | 0.0403 |
| LIVRNOT01 | liver, 49 M | 2 | 0.0397 |
| COLNTUT03 | colon tumor, 62 M, match to COLNNOT16 | 2 | 0.0392 |
| CRBLNOT01 | brain, cerebellum, 69 M | 2 | 0.0391 |
| ADENINB01 | adenoid, inflamed, 3y | 2 | 0.0381 |
| TLYMNOR01 | lymphocytes (non-adher PBMNC), 24 M, RP | 1 | 0.0379 |
| STOMTUT01 | stomach tumor, 52 M, match to STOMNOT02 | 1 | 0.0368 |
| BRAINOT04 | brain, choroid plexus, hemorrhage, 44 M | 1 | 0.0356 |
| PROSNOT07 | prostate, 69 M, match to PROSTUT05 | 1 | 0.0348 |
| BRAITUT02 | brain tumor, metastasis, 58 M | 2 | 0.0340 |
| TONSNOT01 | tonsil, hyperplasia, 6 M | 1 | 0.0339 |
| PROSNOT20 | prostate, hyperplasia, 65 M, match to PROSTUT12 | 1 | 0.0336 |
| SINTBST01 | small intestine, ileum, Crohn's, 18 F | 2 | 0.0336 |
| LNODNOT02 | lymph nodes, 42 F | 1 | 0.0335 |
| HMC1NOT01 | HMC-1 mast cell line, 52 F | 1 | 0.0334 |

FIGURE 13G

| | | |
|---|---|---|
| MMLR3DT01 | macrophages (adher PBMNC), M/F, 72-hr MLR | 1 | 0.0332 |
| SPLNFEM01 | spleen, fetal, WM | 1 | 0.0332 |
| TBLYNOT01 | T-B lymphoblast cell line, leukemia | 1 | 0.0326 |
| LPARNOT02 | parotid gland, 70 M | 1 | 0.0324 |
| BRAITUT08 | brain tumor, astrocytoma, 47 M | 2 | 0.0293 |
| PANCNOT05 | pancreas, 2 M | 2 | 0.0292 |
| PROSTUT05 | prostate tumor, 69 M, match to PROSNOT07 | 2 | 0.0290 |
| DUODNOT01 | small intestine, duodenum, 41 F | 1 | 0.0287 |
| STOMTUT02 | stomach tumor, lymphoma, 68 F | 1 | 0.0284 |
| TESTTUT02 | testicular tumor, 31 M | 1 | 0.0278 |
| SINTNOT13 | small intestine, ileum, ulcerative cholitis, 25 F | 1 | 0.0275 |
| HYPONOB01 | hypothalamus, 16-75 M/F | 1 | 0.0272 |
| BMARNOT02 | bone marrow, 16-70 M/F | 1 | 0.0270 |
| BRAINOM03 | brain, 55 M, NORM, WM | 1 | 0.0270 |
| KIDNTUT01 | kidney tumor, Wilms, 8m F | 1 | 0.0267 |
| PROSTUT08 | prostate tumor, 60 M, match to PROSNOT14 | 1 | 0.0266 |
| COLNNOT23 | colon, 16 M | 1 | 0.0264 |
| BRAITUT13 | brain tumor, meningioma, 68 M | 1 | 0.0262 |
| LEUKNOT03 | white blood cells, 27 F | 1 | 0.0262 |
| BRAITUT07 | brain tumor, left frontal, 32 M | 1 | 0.0259 |
| LIVSFEM03 | liver/spleen, fetal M, NORM, WM | 1 | 0.0256 |
| STOMFET01 | stomach, fetal F | 1 | 0.0255 |
| LIVRNOM01 | liver, 49 M, WM | 1 | 0.0254 |
| TLYMNOT02 | lymphocytes (non-adher PBMNC), M/F | 1 | 0.0254 |
| TMLR3DT01 | lymphocytes (non-adher PBMNC), M, 96-hr MLR | 1 | 0.0229 |
| HNT2NOT01 | hNT2 cell line, teratocarcinoma, control | 1 | 0.0173 |
| UCMCL5T01 | mononuclear cells, treated IL-5 | 1 | 0.0125 |

FIGURE 13H

HUMAN LIM PROTEINS

FIELD OF THE INVENTION

This invention relates to nucleic acid and amino acid sequences of novel human LIM proteins and to the use of these sequences in the diagnosis, prevention, and treatment of disease.

BACKGROUND OF THE INVENTION

The LIM domain is a cysteine-rich motif which was first defined in the proteins Lin-11 from *C. elegans* (Freyd, G. et al. (1990) Nature 344:876–879), insulin gene enhancer binding protein ISL1 from rat (Karlsson, O. et al. (1990) Nature 344:879–882), and Mec-3 from *C. elegans* (Way, J. C. et al. (1 988) Cell 54:5–16). The name LIM is derived from the first letter of the names of these three proteins.

The sequence of the LIM domain is highly conserved among proteins found in different tissues and across a variety of species, which is an indication of the functional importance of this domain (Sanchez-Garcia, I. et al. (1994) Trends Genet. 10:315–320). Two main classes of LIM proteins are known. One class consists of proteins that, like Lin-11, ISL1 and Mec-3, contain two LIM domains plus a homeodomain and are thus designated LIM-HD proteins. The second class of LIM proteins consists of one or more LIM domains without a homeodomain and are thus designated "LIM-only" proteins.

A LIM domain is defined by a conserved consensus amino acid sequence (Wang, X. et al. (1992) J. Biol. Chem. 267:9176–9184). The domain consists of two adjacent zinc-finger motifs. Two zinc ions bind to a LIM domain, one per zinc finger. LIM domains function as protein-binding interfaces (Schmeichel, K. L. et al. (1994) Cell 79:211–219) and thus may act as cofactors in cell signaling.

Some LIM proteins exhibit oncogenic activity while other members of this diverse group may act as tumor suppressor molecules. The rhombotin genes (RBTN1 and RBTN2) encode LIM proteins which have been implicated in the control of the neoplastic phenotype. RBTN2, identified in childhood T cell acute lymphoblastic leukemia (Boehm, T. et al. (1988) EMBO J. 7:385–394), is essential for erythroid cell development. A homozygous null mutation in RBTN2 results in failure of yolk sac erythropoesis and embryonic death (Warren, A. J. et al. (1994) Cell 78:45–57). In transgenic mice, cell-specific overexpression of RBTN1 or RBTN2 results in the generation of acute lymphoblastic lymphomas at low frequency (Fisch, P. et al. (1992) Oncogene 7:2389–2397; McGuire, E. A. et al. (1992) Mol. Cell Biol. 12:4186–4196).

Human cysteine-rich protein (CRP) is widely expressed in a variety of tissues. Its expression is induced shortly after serum stimulation of fibroblasts in the $G_o$ growth-arrest phase of the cell cycle. The serum induction kinetics of CRP closely parallel those of the c-myc oncogene, which suggests that these two genes respond to the same regulatory pathways and may share transcription control features (Wang et al, supra). CRP is thus proposed to be a primary response gene induced as the cell transits from $G_o$ to $G_1$ or progresses from the S phase of the cell cycle, and is proposed to act as an oncogene.

Muscle LIM proteins (MLP) are involved in regulating cell-specific gene expression in heart and skeletal muscle. The expression of human MLP and the Drosophila homolog DMLP1 coincide with the differentiation of myoblasts into muscle cells. Overexpression of MLP in C2 myoblasts potentiates myogenic cell differentiation, whereas expression of antisense MLP RNA retards myoblast differentiation (Arber, S. et al. (1994) Cell 79:221–231).

Smooth muscle LIM protein (smLIM) from rat is expressed preferentially in aortic smooth muscle cells. Like MLP, it is a developmentally regulated nuclear protein. SmLIM mRNA levels decrease in vivo in response to vessel wall injury during periods of maximal smooth muscle proliferation (Jain, M. K. etal. (1996) J. Biol. Chem. 271:10194–10199).

Reversion-induced LIM (RIL) protein from rat is highly expressed in fibroblasts and is down-regulated in H-ras transformed cells. Expression of RIL is restored in phenotypic revertants derived from H-ras transformed cells. RIL is thus proposed to be involved in the maintenance of normal cell growth (Kiess, M. et al. (1995) Oncogene 10:61–68). RIL is expressed in brain, heart, testes and variety of epithelia. The pattern of RIL protein expression suggests a physiological function in epithelial cells and in postmitotic neurons of the brain.

CLP36 protein is highly expressed in normal rat hepatocytes and is down-regulated in hypoxic hepatocytes. The relationship of this down-regulation to hypoxic injury is not understood. CLP36 is found in a wide variety of tissues, at high abundance in heart, lung and liver, moderate abundance in spleen and skeletal muscle, and at extremely low abundance in testis and brain (Wang H. et al. (1995) Gene 165:267–271).

The discovery of polynucleotides encoding LIM proteins, and the protein molecules themselves, presents the opportunity to investigate physiological processes relating to the control of cellular differentiation, proliferation, and response to tissue injury. Discovery of novel LIM proteins and the polynucleotides encoding them satisfies a need in the art by providing new diagnostic or therapeutic compositions directed toward diseases relating to cell damage and abnormal cell growth and proliferation such as arteriosclerosis and cancer.

SUMMARY OF THE INVENTION

The present invention features three novel human LIM proteins, designated individually as HLIM-1, HLIM-2 and HLIM-3 and collectively as HLIM, and characterized as having similarity to the LIM proteins CRP and MLP from human and smLIM, CLP36 and RIL from rat.

Accordingly, the invention features substantially purified HLIM proteins HLIM-1, HLIM-2, and HLIM-3 having chemical homology to the LIM proteins above and as shown in amino acid sequences SEQ ID NO:1, SEQ ID NO:3, and SEQ ID NO:5, respectively.

One aspect of the invention features isolated and substantially purified polynucleotides that encode HLIM proteins HLIM-1, HLIM-2, and HLIM-3. In a particular aspect, the polynucleotides are the nucleotide sequences of SEQ ID NO:2, SEQ ID NO:4, or SEQ ID NO:6, respectively.

The invention also relates to a polynucleotide sequence comprising the complement of SEQ ID NO:2, SEQ ID NO:4, SEQ ID NO:6, or variants thereof. In addition, the invention features polynucleotide sequences which hybridize under stringent conditions to SEQ ID NO:2, SEQ ID NO:4, or SEQ ID NO:6.

The invention additionally features nucleic acid sequences encoding polypeptides, oligonucleotides, peptide nucleic acids (PNA), fragments, portions or antisense molecules thereof, and expression vectors and host cells comprising polynucleotides that encode HLIM. The present invention also features antibodies which bind specifically to HLIM, and pharmaceutical compositions comprising substantially purified HLIM. The invention also features the use of agonists and antagonists of HLIM.

BRIEF DESCRIPTION OF THE FIGURES

FIG. 1A and 1B show the amino acid sequence (SEQ ID NO: 1) and nucleic acid sequence (SEQ ID NO:2) of HLIM-1. The alignment was produced using MACDNASIS PRO™ software (Hitachi Software Engineering Co., Ltd., San Bruno, Calif.).

FIG. 2A and 2B show the amino acid sequence (SEQ ID NO:3) and nucleic acid sequence (SEQ ID NO:4) of HLIM-2.

FIG. 3A and 3B show the amino acid sequence (SEQ ID NO:5) and nucleic acid sequence (SEQ ID NO:6) of HLIM-3.

FIG. 4 shows the amino acid sequence alignments among HLIM-1 (SEQ ID NO: 1), human CRP (GI 118161; SEQ ID NO:7) and MLP (GI 1234841; SEQ ID NO:8), and rat smLIM (GI 1314351; SEQ ID NO:9). The alignment was produced using the multisequence alignment program of DNASTAR™ software (DNASTAR Inc, Madison Wis.).

FIG. 5 shows the amino acid sequence alignments among HLIM-2 (SEQ ID NO:3), rat CLP36 (GI 1020151; SEQ ID NO:10) and rat RIL (GI 887580; SEQ ID NO:11).

FIG. 6 shows the amino acid sequence alignments among IILIM-3 (SEQ ID NO:5), rat proteins CLP36 (GI 1020151; SEQ ID NO:10) and rat RIL (GI 887580; SEQ ID NO: 11).

FIG. 12 shows the northern analysis for SEQ ID NO:2. The northern analysis was produced electronically using LIFESEQTM database (Incyte Pharmaceuticals, Inc., Palo Alto, Calif.).

FIG. 13 shows the northern analysis for SEQ ID NO:6.

DESCRIPTION OF THE INVENTION

Figure 7:
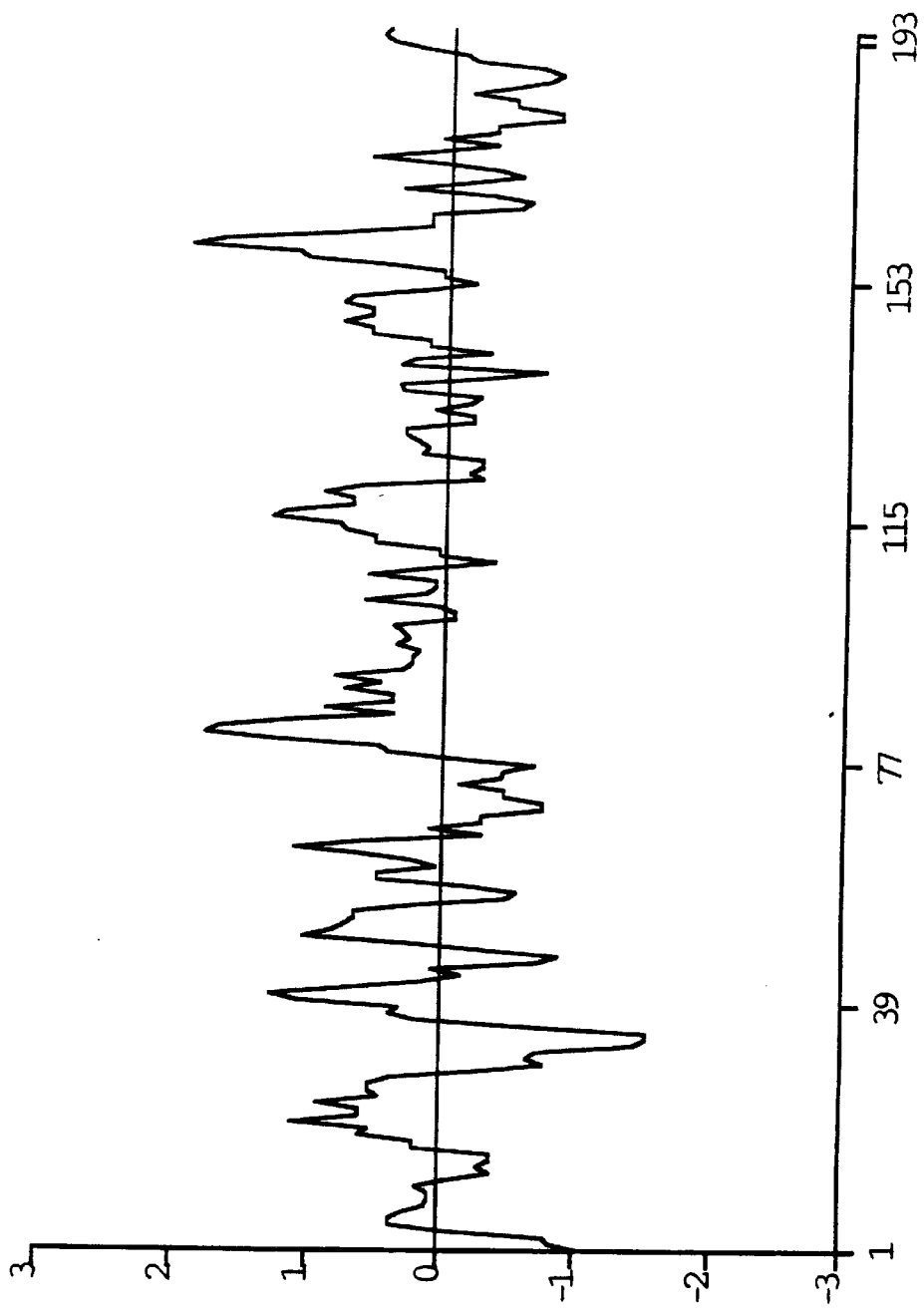
FIG. 7 shows the hydrophobicity plot (MACDNASIS PRO software) for HLIM-1, SEQ ID NO: 1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HLIM, as used herein, refers to the amino acid sequences of substantially purified HLIM obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™, a PCR kit (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of HLIM, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HLIM, or any oligopeptide thereof, to induce a specific immune response in appropriate animals or cells and to bind with specific antibodies.

The term "agonist", as used herein, refers to a molecule which, when bound to HLIM, causes a change in HLIM which modulates the activity of HLIM. Agonists may include proteins, nucleic acids, carbohydrates, or any other molecules which bind to HLIM. The terms "antagonist" or "inhibitor", as used herein, refer to a molecule which, when bound to HLIM, blocks the biological or immunological activity of HLIM. Antagonists and inhibitors may include proteins, nucleic acids, carbohydrates, or any other molecules which bind to HLIM.

The term "modulate", as used herein, refers to a change or an alteration in the biological activity of HLIM. Modulation may be an increase or a decrease in protein activity, a change in binding characteristics, or any other change in the biological, functional or immunological properties of HLIM.

The term "mimetic", as used herein, refers to a molecule, the structure of which is developed from knowledge of the structure of HLIM or portions thereof and, as such, is able to effect some or all of the actions of LIM protein-like molecules.

The term "derivative", as used herein, refers to the chemical modification of a nucleic acid encoding HLIM or the encoded HLIM. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by basepairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second noncomplementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HLIM-1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HLIM or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding HLIM in a sample and thereby correlates with expression of the transcript from the polynucleotide encoding the protein.

"Alterations" in the polynucleotide of SEQ ID NO:2, SEQ ID NO:4, or SEQ ID NO:6, as used herein, comprise any alteration in the sequence of polynucleotides encoding HLIM including deletions, insertions, and point mutations that may be detected using hybridization assays. Included within this definition is the detection of alterations to the genomic DNA sequence which encodes HLIM (e.g., by alterations in the pattern of restriction fragment length polymorphisms capable of hybridizing to SEQ ID NO:2, SEQ ID NO:4, or SEQ ID NO:6), the inability of a selected fragment of SEQ ID NO:2, SEQ ID NO:4, or SEQ ID NO:6 to hybridize to a sample of genomic DNA (e.g., using allele-specific oligonucleotide probes), and improper or unexpected hybridization, such as hybridization to a locus other than the normal chromosomal locus for the polynucleotide sequence encoding HLIM (e.g., using fluorescent in situ hybridization (FISH) to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind HLIM polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of three novel human LIM proteins (HLIM-1, HLIM-2, and HLIM-3, collectively referred to as HLIM), the polynucleotides encoding HLIM, and the use of these compositions for the diagnosis, prevention, or treatment of cancer, arteriosclerosis, or other diseases or conditions relating to abnormal regulation of cell growth.

Nucleic acids encoding the human HLIM-1 of the present invention were first identified in Incyte Clone 305288 from an adult heart tissue cDNA library (HEARNOT01) through a computer-generated search for amino acid sequence alignments. A consensus sequence, SEQ ID NO:2, was derived from the following overlapping and/or extended nucleic acid sequences (cDNA library from which derived): Incyte Clones 305288, 305719, 305804, 307231 (HEARNOT01); 532714 (BRAINOT03); 963636 (BRSTTUT03); 1004370 (BRSTNOT03); 1266381 (BRAINOT09); and 1436648 (PANCNOT08).

Nucleic acids encoding the human HLIM-2 of the present invention were first identified in Incyte Clone 267324 from an hNT2 cell line cDNA library (HNT2NOT01) through a computer-generated search for amino acid sequence alignments. A consensus sequence, SEQ ID NO:4, was derived from the following overlapping and/or extended nucleic acid sequences (cDNA library from which derived): Incyte Clones 970132 (MUSCNOT02); 778312 (COLNNOT05); 1291737 (PGANNOT03); 1504324 (BRAITUT07); 922412

(RATRNOT02); 13493 14 (LATRTUT02); and 267324 (HNT2NOT01).

Nucleic acids encoding the human HLIM-3 of the present invention were first identified in Incyte Clone 1429619, from an ileum tissue cDNA library (SINTBST01) through a computer-generated search for amino acid sequence alignments. A consensus sequence, SEQ ID NO:6, was derived from the following overlapping and/or extended nucleic acid sequences (cDNA library from which derived): Incyte Clones 1429619 (SINTBST01); 425837 (BLADNOT01); 1823189 (GBLATUT01); 922744 (RATRNOT02); 352494 (LVENNOT 01); and 766348 (LUNGNOT04).

Figure 8:
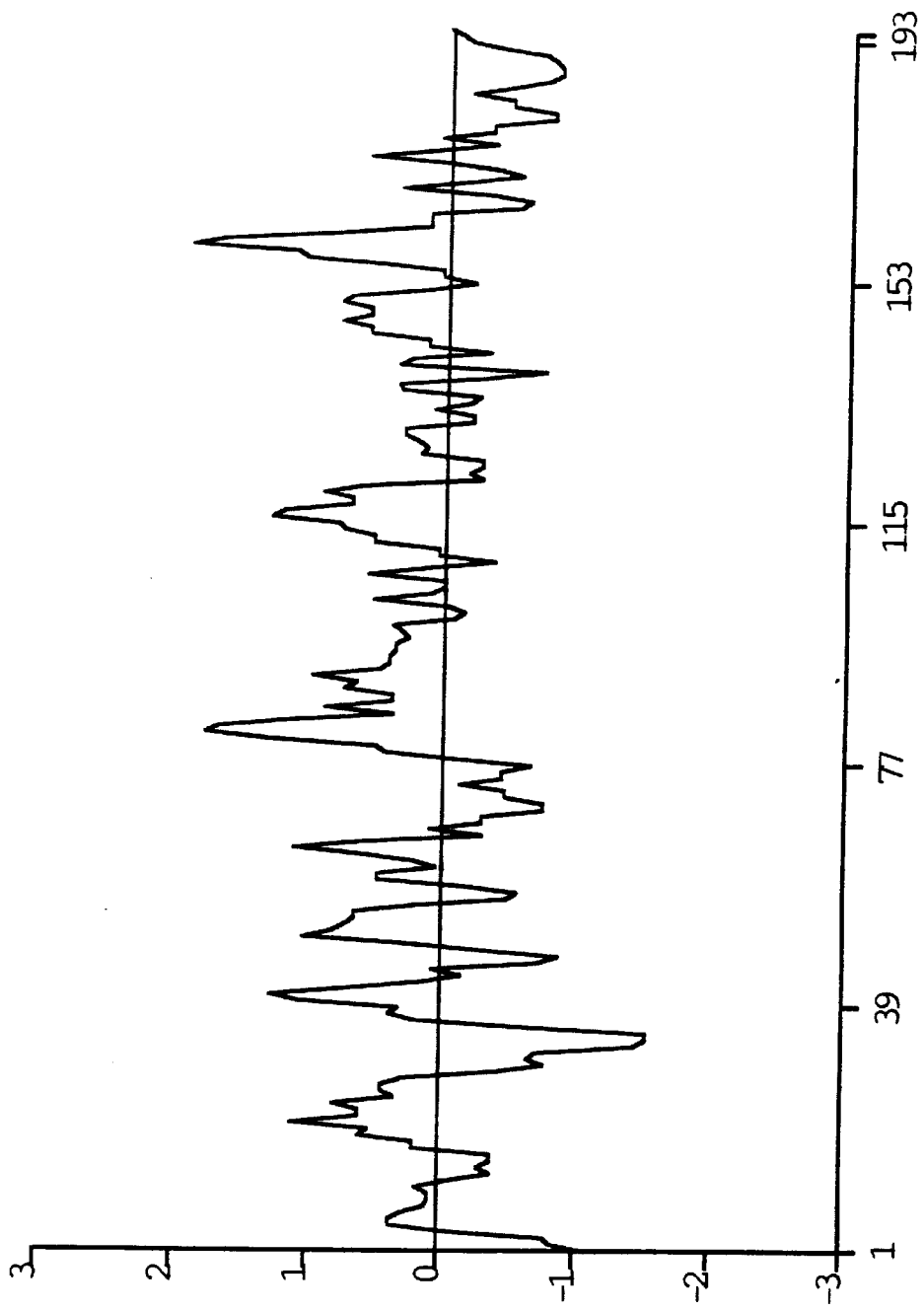
FIG. 8 shows the hydrophobicity plot for rat smLIM, SEQ ID NO:9.

In one embodiment, the invention encompasses the novel human LIM protein HLIM-1, a polypeptide comprising the amino acid sequence of SEQ ID NO: 1, as shown in FIG. 1A and 1B. HLIM-1 is 193 amino acids in length and contains a potential nuclear localization motif comprising amino acid residue 64–69 of SEQ ID NO:1. In addition, HLIM-1 contains a potential protein kinase C phosphorylation site at $T_{159}$ and a potential tyrosine kinase phosphorylation site at $Y_{121}$. As shown in FIG. 4, HLIM-1 has chemical and structural homology with human CRP (GI 1 18161; SEQ ID NO:7) human MLP (GI 1234841; SEQ ID NO:8), and rat smLIM (GI 1314351; SEQ ID NO:9). In particular, HLIM-1 shares 81%, 67%, and 97% identity with human CRP, human MLP and rat smLIM, respectively. As illustrated by FIGS. 7 and 8, HLIM and rat smLIM have similar hydrophobicity plots. HLIM-1 contains two LIM domains spanning positions $C_{10}$ to $C_{61}$, and $C_{119}$ to $C_{170}$. The amino acid motifs which define these domains are precisely conserved in CRP, MLP and smLIM. From the northern analysis (FIG. 12), HLIM-1 is abundantly expressed in heart and bladder tissue CDNA libraries, which suggests a specific role in smooth muscle cell and possibly cardiac muscle cell function. In addition, HLIM-1 is found in several fetal tissue libraries, which suggests a developmental role for this molecule. Expression of HLIM-1 appears to decrease in tumor associated tissues; for instance, HLIM-1 expression is decreased in 20-fold in heart myoma tumor tissue as compared to normal heart tissue.

Figure 9:
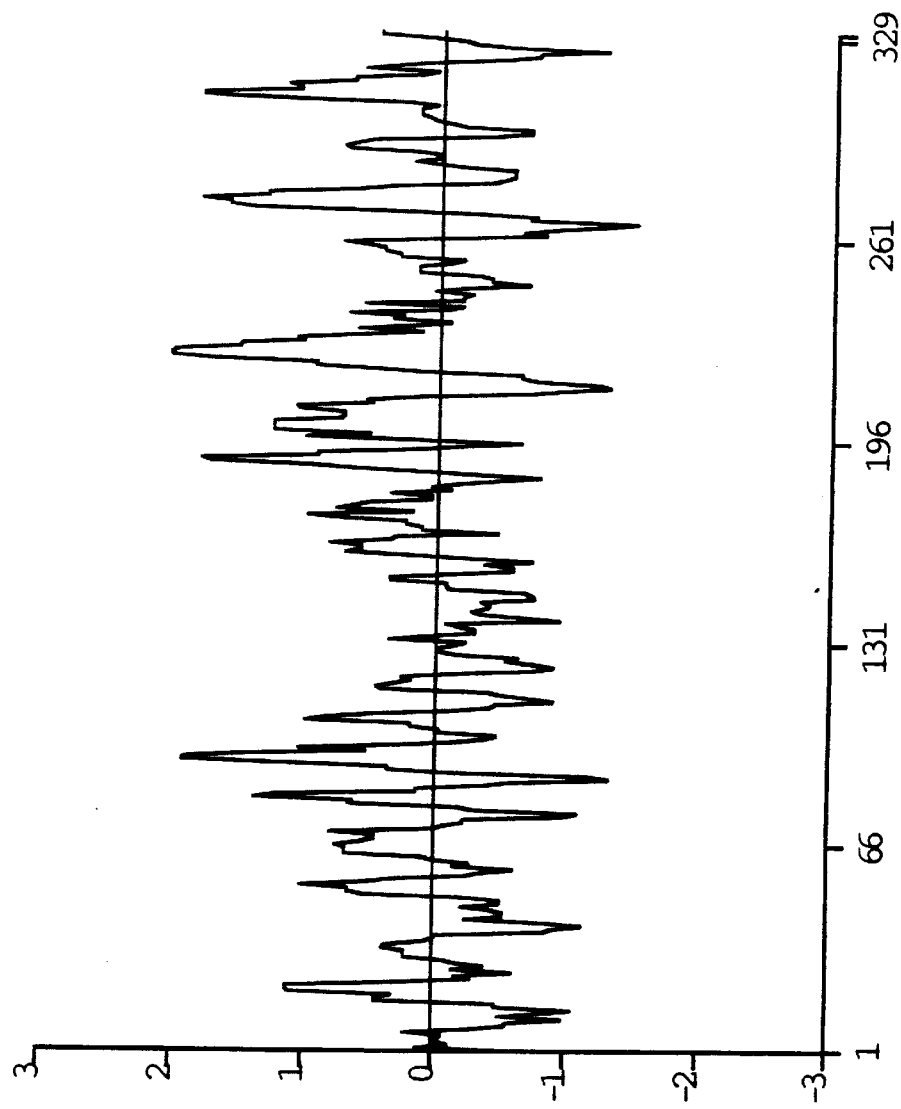
FIG. 9 shows the hydrophobicity plot for HLIM-2, SEQ ID NO:3.
Figure 11:
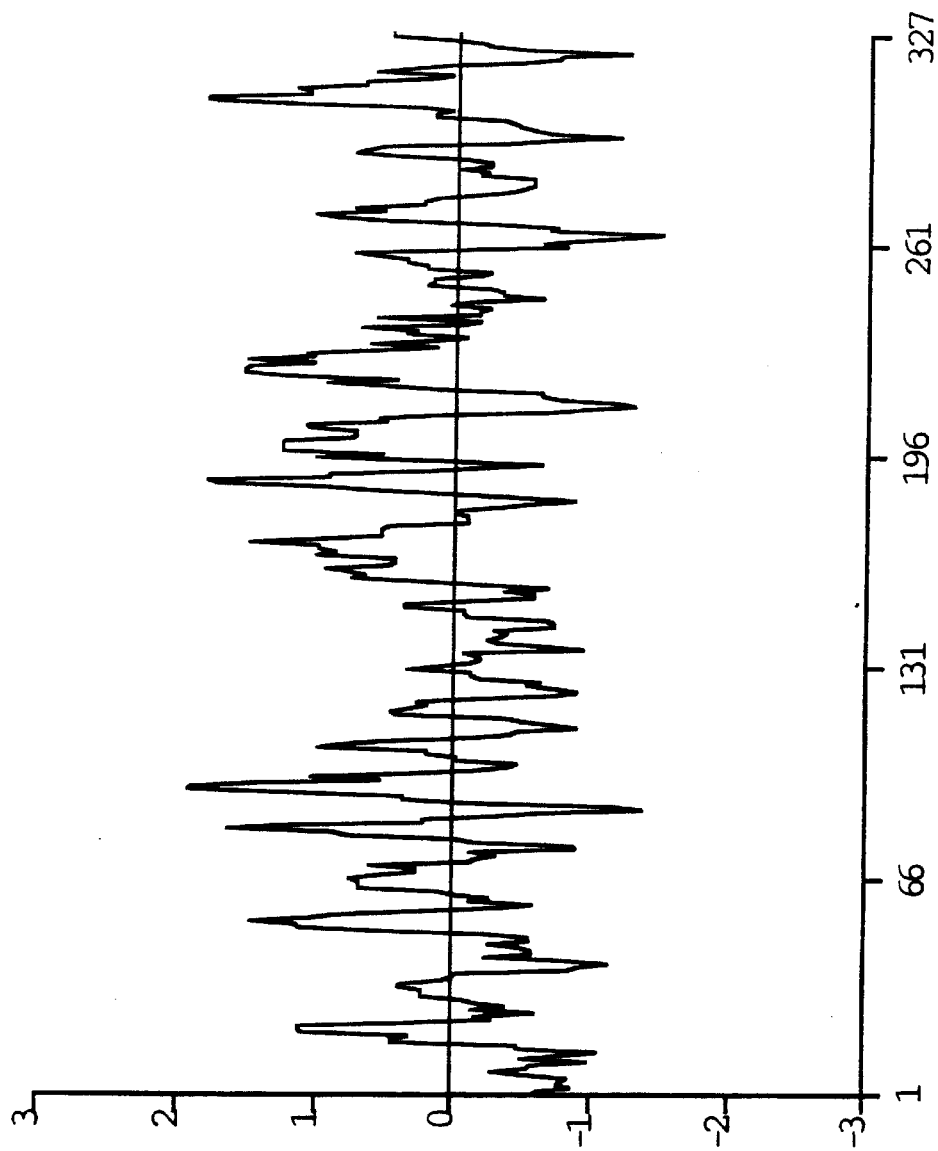
FIG. 11 shows the hydrophobicity plot for rat CLP36, SEQ ID NO:10.

In another embodiment, the invention encompasses the novel human LIM protein HLIM-2, a polypeptide comprising the amino acid sequence of SEQ ID NO:3, as shown in FIGS. 2A and 2B. HLIM-2 is 329 amino acids in length. As shown in FIG. 5, HLIM-2 has chemical and structural homology with rat CLP36 (GI 1020151; SEQ ID NO:10) and rat RIL (GI 887580; SEQ ID NO: 11). In particular, HLIM-2 and CLP36 share 88% identity, whereas HLIM-2 and RIL share 44% identity. As illustrated by FIGS. 9 and 11, HLIM-2 and CLP36 have rather similar hydrophobicity plots. HLIM-2 contains a single LIM domain, defined by amino acids $C_{260}$, $C_{263}$, $H_{280}$, $C_{283}$, $C_{286}$, $C_{289}$, $C_{307}$ and $H_{310}$, which is precisely conserved in CLP36 and RIL. Northern analysis (not shown) reveals the expression of this sequence in 222 cDNA libraries prepared from a wide variety of tissues, with highest abundance in breast, ovary, uterus, lung, heart, skeletal muscle, and synovium. The expression of sequences encoding HLIM-2 appears to be diminished in tumor-associated tissues. Only one of the 40 libraries which express the highest abundance of HLIM-2 are tumor-associated. In particular, tumor-associated tissue from breast and lung contain significantly less HLIM-2 mRNA than normal breast and lung tissue.

In an additional embodiment, the invention encompasses the novel human LIM protein HLIM-3, a polypeptide comprising the amino acid sequence of SEQ ID NO:5, as shown in FIGS. 3A and 3B. HLIM-3 is 316 amino acids in length.

Figure 10:
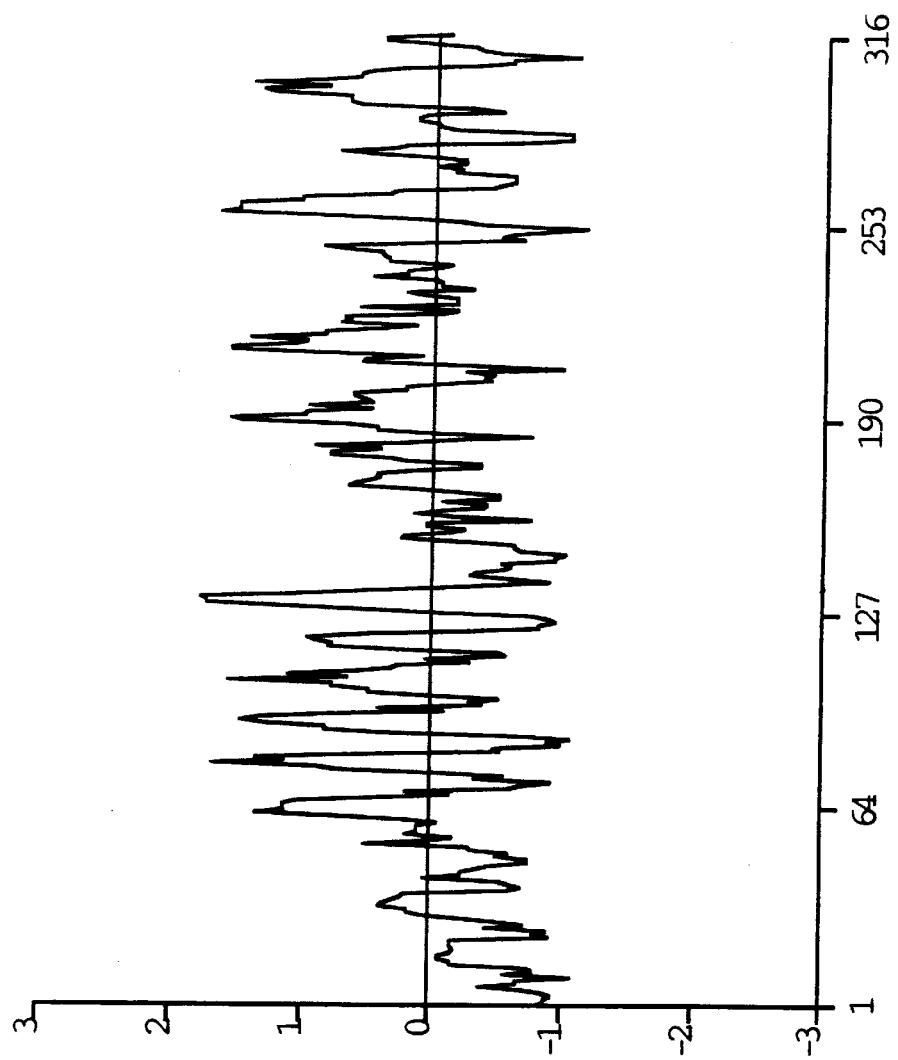
FIG. 10 shows the hydrophobicity plot for HLIM-3, SEQ ID NO:5.

As shown in FIG. 6, HLIM-3 has chemical and structural homology with rat CLP36 (GI 102015 1; SEQ ID NO: 10) and rat RIL (GI 887580; SEQ ID NO: 11). In particular, HLIM-3 and CLP36 share 53% identity, whereas HLIM-3 and RIL share 45% identity. As illustrated by FIGS. 10 and 11, HLIM-3 and CLP36 have rather similar hydrophobicity plots. The single LIM domain of HLIM-3, defined by amino acids $C_{246}$, $C_{249}$, $H_{266}$, $C_{269}$, $C_{272}$, $C_{275}$, $C_{293}$, and $H_{296}$, is precisely conserved in CLP36 and RIL. Northern analysis (FIG. 13) shows the expression of this sequence is most abundant in skeletal muscle. HLIM-3 encoding sequences are also expressed in cDNA libraries related to smooth and cardiac muscle including heart, ovary, stomach, bladder, prostate, breast, and colon. The expression of sequences encoding HLIM-3 appears to be diminished in tumor-associated tissues; of the 43 libraries which express HLIM-3, only 5 are tumor-associated. The invention also encompasses HLIM variants. A preferred HLIM variant is one having at least 80%, and more preferably 90%, amino acid sequence similarity to the HLIM amino acid sequence (SEQ ID NO:1, SEQ ID NO:3, or SEQ ID NO:5). A most preferred HLIM variant is one having at least 95% amino acid sequence similarity to SEQ ID NO: 1, SEQ ID NO:3, or SEQ ID NO:5.

The invention also encompasses polynucleotides which encode HLIM. Accordingly, any nucleic acid sequence which encodes the amino acid sequence of HLIM can be used to generate recombinant molecules which express HLIM. In a particular embodiment, the invention encompasses the polynucleotide comprising the nucleic acid of SEQ ID NO:2, SEQ ID NO:4, or SEQ ID NO:6 as shown in FIGS. 1A, 1B, 2A, 2B, 3A and 3B.

It will be appreciated by those skilled in the art that as a result of the degeneracy of the genetic code, a multitude of nucleotide sequences encoding HLIM, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HLIM, and all such variations are to be considered as being specifically disclosed.

Although nucleotide sequences which encode HLIM and its variants are preferably capable of hybridizing to the nucleotide sequence of the naturally occurring HLIM under appropriately selected conditions of stringency, it may be advantageous to produce nucleotide sequences encoding HLIM or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HLIM and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HLIM and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HLIM or any portion thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency. Hybridization conditions are based on the melting temperature (Tm) of the nucleic acid binding complex or probe, as taught in Kimmel, A. R. (1987; Methods Enzymol. Vol. 152), and may be used at a defined stringency.

Altered nucleic acid sequences encoding HLIM which are encompassed by the invention include deletions, insertions, or substitutions of different nucleotides resulting in a polynucleotide that encodes the same or a functionally equivalent HLIM. The encoded protein may also contain deletions, insertions, or substitutions of amino acid residues which produce a silent change and result in a functionally equivalent HLIM. Deliberate amino acid substitutions may be made on the basis of similarity in polarity, charge, solubility, hydrophobicity, hydrophilicity, and/or the amphipathic nature of the residues as long as the biological activity of HLIM is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HLIM. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE™, DNA polymerase (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The polynucleotide sequence encoding HLIM may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER™ libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HLIM, or fusion proteins or functional equivalents thereof, may be used in recombinant DNA molecules to direct expression of HLIM in appropriate host cells. Due to the inherent degeneracy of the genetic code, other DNA sequences which encode substantially the same or a functionally equivalent amino acid sequence may be produced and these sequences may be used to clone and express HLIM.

As will be understood by those of skill in the art, it may be advantageous to produce HLIM-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HLIM coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HLIM may be ligated to a heterologous sequence to encode a fusion protein. For example, to screen peptide libraries for inhibitors of HLIM activity, it may be useful to encode a chimeric HLIM protein that can be recognized by a commercially available antibody. A fusion protein may also be engineered to contain a cleavage site located between a HLIM encoding sequence and the heterologous protein sequence, so that HLIM may be cleaved and purified away from the heterologous moiety.

In another embodiment, the coding sequence of HLIM may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the HLIM amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of HLIM, or any part thereof, may be altered during direct synthesis and/or combined using chemical methods with sequences from other proteins, or any part thereof, to produce a variant polypeptide.

In order to express a biologically active HLIM, the nucleotide sequence encoding HLIM or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HLIM coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express a HLIM coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT™ phagemid (Stratagene, LaJolla, Calif.) or pSPORT1™ plasmid (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HLIM, vectors based on SV40 or EBV may be used with an appropriate selectable marker.

In bacterial systems, a number of expression vectors may be selected depending upon the use intended for HLIM. For example, when large quantities of HLIM are needed for the induction of antibodies, vectors which direct high level expression of fusion proteins that are readily purified may be used. Such vectors include, but are not limited to, the multifunctional *E. coli* cloning and expression vectors such as BLUESCRIPT™) (Stratagene), in which the sequence encoding HLIM may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HLIM may be driven by any of a number of promoters. For example, viral promoters such as the 35S and 19S promoters of CaMV may be used alone or in combination with the omega leader sequence from TMV (Takamatsu, N. (1987) EMBO J. 6:307–31 1). Alternatively, plant promoters such as the small subunit of RUBISCO or heat shock promoters may be used (Coruzzi, G. et al. (1 984) EMBO J. 3:1671–1680; Broglie, R. et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HLIM. For example, in one such system, *Autographa califomica* nuclear polyhedrosis virus (AcNPV) is used as a vector to express foreign genes in *Spodoptera frugiperda* cells or in Trichoplusia larvae. The sequence encoding HLIM may be cloned into a non-essential region of the virus, such as the polyhedrin gene, and placed under control of the polyhedrin promoter. Successful insertion of HLIM will render the polyhedrin gene inactive and produce recombinant virus lacking coat protein. The recombinant viruses may then be used to infect, for example, *S. frugiperda* cells or Trichoplusia larvae in which IILIM may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HLIM may be ligated into an adenovirus transcription/translation complex consisting of the late promoter and tripartite leader sequence. Insertion in a non-essential E1 or E3 region of the viral genome may be used to obtain a viable virus which is capable of expressing HLIM in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HLIM. Such signals include the ATG initiation codon and adjacent sequences. In cases where sequences encoding HLIM, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HLIM may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 1 1:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HLIM is inserted within a marker gene sequence, recombinant cells containing sequences encoding HLIM can be identified by the absence of marker gene function. Alternatively, a marker gene can be placed in tandem with a sequence encoding HLIM under the control of a single promoter. Expression of the marker gene in response to induction or selection usually indicates expression of the tandem gene as well.

Alternatively, host cells which contain the coding sequence for HLIM and express HLIM may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of the nucleic acid or protein.

The presence of the polynucleotide sequence encoding HLIM can be detected by DNA—DNA or DNA-RNA hybridization or amplification using probes or portions or fragments of polynucleotides encoding HLIM. Nucleic acid amplification based assays involve the use of oligonucleotides or oligomers based on the HLIM-encoding sequence to detect transformants containing DNA or RNA encoding HLIM. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HLIM, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HLIM is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HLIM include oligolabeling, nick translation, end-labeling or PCR amplification using a labeled nucleotide. Alternatively, the sequence encoding HLIM, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharnacia & Upjohn (Kalamazoo, Miss.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HLIM may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HLIM may be designed to contain signal sequences which direct secretion of HLIM through a prokaryotic or eukaryotic cell membrane. Other recombinant constructions may be used to join sequences encoding HLIM to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HLIM may be used to facilitate purification. One such expression vector provides for expression of a fusion protein containing HLIM and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying HLIM from the fusion protein. A discussion of vectors which contain fusion proteins is provided in Kroll, D. J. et al. (1993; DNA Cell Biol. 12:441–453).

In addition to recombinant production, fragments of HLIM may be produced by direct peptide synthesis using solid-phase techniques (cf Stewart et al. (1969) Solid-Phase Peptide Synthesis, W. H. Freeman Co., San Francisco, Calif.; Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HLIM may be chemically synthesized separately and combined using chemical methods to produce the full length molecule.

Therapeutics

In another embodiment of the invention, HLIM or fragments thereof may be used for therapeutic purposes.

The rationale for the therapeutic use of the HLIM sequences disclosed herein are based in part on the chemical and structural homology among HLIM-1 human MLP and rat smLIM, and among HLIM-2, HLIM-3, rat CLP36 and rat RIL. Furthermore, the expression patterns of HLIM suggest a role in promoting or maintaining normal tissue growth and differentiation. HLIM-1 and HLIM-3 are expressed primarily in muscle tissues, whereas HLIM-2 is expressed in a wide variety of tissues.

Since expression of HLIM appears to be negatively correlated with cancer (FIGS. 12 and 13, and as discussed above), vectors containing the nucleic acid sequence encoding HLIM may be used to promote differentiation and to restore tumor cells to a normal phenotype. These vectors could be delivered into tumors or cancerous cells using technologies well known in the art or as an adjunct to biopsy of the cancer. Control of HLIM activity as a novel approach to cancer treatment may be especially useful in combination therapy with other, conventional chemotherapeutic agents. Such combinations of therapeutic agents having different cellular mechanisms of action often have synergistic effects allowing the use of lower effective doses of each agent and lessening side effects.

In another embodiment, vectors expressing antisense, and antagonists or inhibitors of the protein may be used to induce proliferation or regeneration of cells, tissues and organs which are not readily regenerated. Regeneration and development of nerve, pancreatic, epithelial, etc. tissue will involve supplying various molecules including HLIM antagonists in drug regimes that allow cell division to occur. Small amounts of new functional tissue have the capacity to greatly improve the quality of life for victims of accidents or degenerative diseases. Furthermore, HLIM antagonists may be useful in stimulating skin production in vitro or ex vivo for use in skin grafts.

In another embodiment, antagonists which block or modulate the effect of HLIM may be used in those situations where such inhibition is therapeutically desirable. Such antagonists or inhibitors may be produced using methods which are generally known in the art, and include particularly the use of purified HLIM to produce antibodies or to screen libraries of pharmaceutical agents for those which specifically bind HLIM. For example, in one aspect, antibodies which are specific for HLIM may be used directly as an antagonist, or indirectly as a targeting or delivery mechanism for bringing a pharmaceutical agent to cells or tissue which express HLIM.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HLIM or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HLIM have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HLIM amino acids may be fused with those of another protein such as keyhole limpet hemocyanin and antibody produced against the chimeric molecule.

Monoclonal antibodies to HLIM may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1 985) *Monoclonal Antibodies and Cancer Therapy,* Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HLIM-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, et al. (1989) Proc. Natl. Acad. Sci. 86: 3833–3837; Winter, G. et al. (1991) Nature 349:293–299).

Antibody fragments which contain specific binding sites for HLIM may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HLIM and its specific antibody. A two-site, monoclonal-based immunoassay utilizing monoclonal antibodies reactive to two non-interfering HLIM epitopes is preferred, but a competitive binding assay may also be employed (Maddox, supra).

In another embodiment of the invention, the polynucleotides encoding HLIM, or any fragment thereof, or antisense sequences, may be used for therapeutic purposes. In one aspect, antisense to the polynucleotide encoding HLIM may be used in situations in which it would be desirable to block the synthesis of the protein. In particular, cells may be transformed with sequences complementary to polynucleotides encoding HLIM. Thus, antisense sequences may be used to modulate HLIM activity, or to achieve regulation of gene function. Such technology is now well known in the art, and sense or antisense oligomers or larger fragments, can be designed from various locations along the coding or control regions of sequences encoding HLIM.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HLIM. These techniques are described both in Sambrook et al. (supra) and in Ausubel et al. (supra).

Genes encoding HLIM can be turned off by transforming a cell or tissue with expression vectors which express high levels of a polynucleotide or fragment thereof which encodes HLIM. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HLIM, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HLIM.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HLIM. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HLIM, antibodies to HLIM, mimetics, agonists, antagonists, or inhibitors of HLIM. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HLIM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HLIM or fragments thereof, antibodies of HLIM, agonists, antagonists or inhibitors of HLIM, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HLIM may be used for the diagnosis of conditions or diseases characterized by expression of HLIM, or in assays to monitor patients being treated with HLIM, agonists, antagonists or inhibitors. The antibodies useful for diagnostic purposes may be prepared in the same manner as those described above for therapeutics. Diagnostic assays for HLIM include methods which utilize the antibody and a label to detect HLIM in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HLIM are known in the art and provide a basis for diagnosing altered or abnormal levels of HLIM expression. Normal or standard values for HLIM expression are established by combining body fluids or cell extracts taken from normal mammalian subjects, preferably human, with antibody to HLIM under conditions suitable for complex formation. The amount of standard complex formation may be quantified by various methods, but preferably by photometric means. Quantities of HLIM expressed in subject samples, control and disease, from biopsied tissues are compared with the standard values. Deviation between standard and subject values establishes the parameters for diagnosing disease.

In another embodiment of the invention, the polynucleotides encoding HLIM may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HLIM may be correlated with disease. The diagnostic assay may be used to distinguish between absence, presence, and excess expression of HLIM, and to monitor regulation of HLIM levels during therapeutic intervention.

In one aspect, hybridization with PCR probes which are capable of detecting polynucleotide sequences, including genomic sequences, encoding HLIM or closely related molecules, may be used to identify nucleic acid sequences which encode HLIM. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HLIM, alleles, or related sequences.

Probes may also be used for the detection of related sequences, and should preferably contain at least 50% of the nucleotides from any of the HLIM encoding sequences. The hybridization probes of the subject invention may be DNA or RNA and derived from the nucleotide sequence of SEQ ID NO:2, SEQ ID NO:4, or SEQ ID NO:6 or from genomic sequence including promoter, enhancer elements, and introns of the naturally occurring HLIM.

Means for producing specific hybridization probes for DNAs encoding HLIM include the cloning of nucleic acid sequences encoding HLIM or HLIM derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HLIM may be used for the diagnosis of conditions or diseases which are associated with expression of HLIM. Examples of such conditions or diseases include cancers of the heart, breast, colon, and prostate, and diseases associated with proliferation of smooth muscle cells such as arteriosclerosis. The polynucleotide sequences encoding HLIM may be used in Southern or northern analysis, dot blot, or other membrane-based technologies; in PCR technologies; or in dip stick, pin, ELISA or chip assays utilizing fluids or tissues from patient biopsies to detect altered HLIM expression. Such qualitative or quantitative methods are well known in the art.

In a particular aspect, the nucleotide sequences encoding HLIM may be useful in assays that detect activation or induction of various cancers, particularly those mentioned above. The nucleotide sequence encoding HLIM may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HLIM in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HLIM, a normal or standard profile for expression is established. This may be accomplished by combining body fluids or cell extracts taken from normal subjects, either animal or human, with a sequence, or a fragment thereof, which encodes IILIM, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides encoding HLIM may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HLIM include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes HLIM may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C.M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HLIM on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11 q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HLIM, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HLIM and the agent being tested, may be measured.

Another technique for drug screening which may be used provides for high throughput screening of compounds having suitable binding affinity to the protein of interest as described in published PCT application WO84/03564. In this method, as applied to HLIM large numbers of different small test compounds are synthesized on a solid substrate, such as plastic pins or some other surface. The test compounds are reacted with HLIM, or fragments thereof, and washed. Bound HLIM is then detected by methods well known in the art. Purified HLIM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HLIM specifically compete with a test compound for binding HLIM. In this manner, the antibodies can be used to detect the presence of any peptide which shares one or more antigenic determinants with HLIM.

In additional embodiments, the nucleotide sequences which encode HLIM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

HEARNOT01

The HEARNOT01 library was constructed from heart tissue obtained from a 56 year-old Caucasian male (Lot No. HAL 194, International Institute for the Advancement of Medicine (IIAM), Exton, Pa.).

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCI cushion using an Beckman SW28 rotor in a Beckman L8–70M Ultracentrifuge (Beckman Instruments) for 18 hours at 25,000 rpm at ambient temperature. The RNA was extracted with acid phenol pH 4.0, precipitated using 0.3M sodium acetate and 2.5 volumes of ethanol, resuspended in RNAse-free water, and DNase treated at 37° C. The RNA extraction was repeated with acid phenol pH 4.0 and precipitated with sodium acetate and ethanol as before. The mRNA was then isolated using the Qiagen OLIGOTEX™ kit, mRNA isolation kit (Qiagen, Inc., Chatsworth, Calif.) and used to construct the cDNA library.

First strand cDNA synthesis was accomplished using an oligo d(T) primer/linker which also contained an Xhol restriction site. Second strand synthesis was performed using a combination of DNA polymerase I, $E.\ coli$ ligase and RNase H, followed by the addition of an EcoRi adaptor to the blunt ended cDNA. The EcoRI adapted, double-stranded cDNA was then digested with Xhol restriction enzyme and fractionated to obtain sequences which exceeded 800 bp in size. The cDNAs were inserted into the LAMBDAZAP™ vector system (Stratagene); then the vector which contained the pBLUESCRIPT™ phagemid (Stratagene) was transformed into $E.\ coli$ host cells strain XLI -BLUEMRF™ (Stratagene).

The phagemid forms of individual cDNA clones were obtained by the in vivo excision process. Enzymes from both pBLUESCRIPT™ and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells SOLR™ (Stratagene). Presence of the phagemid which contained the gene for β-lactamase allowed transformed bacteria to grow on medium containing ampicillin.

HNT2NOT01

The hNT2 cell line exhibits characteristics of a committed neuronal precursor cell which is still at an early stage of development. The HNT2NOT01 cDNA library prepared from this untreated cell line was obtained from Stratagene (Cat. No. 937230). The cDNA library was constructed by essentially the following procedure. cDNAs were primed using oligo d(T) and size fractionated to isolate fragments of 500 bp and larger. Synthetic adapter oligonucleotides were ligated onto the cDNA molecules enabling them to be inserted into the UNI-ZAP™ vector system (Stratagene). The quality of the cDNA library was screened using DNA probes, and then, the pBLUESCRIPT™ phagemid (Stratagene) was excised. Subsequently, the custom-constructed library phage particles were infected into $E\ coli$ host strain XL 1-BLUE™ (Stratagene).

SINTBST01

The SINTBST01 cDNA library was constructed from Crohn's disease affected small intestine tissue obtained from an 18-year-old Caucasian female. This tissue was associated with cDNA library COLNNOT19 which was microscopically normal colon tissue from the same patient. The patient presented with abdominal pain and symptoms of enteritis; the following tissue was excised during anastomosis: 16 cm segment of ileum with 5 cm segment of cecum, and 5.5×0.4 cm of appendix. Crohn's disease was identified involving 15 cm of the small bowel. The cecum and appendix were unremarkable, and the margins were uninvolved. The patient was treated with PRILOXEC™ (omeprazole for abdominal pain; Astra/Merck Group of Merck & Co., Wayne, Pa.); PENTASA™ (mesalamine for colitis; Marion Merrell Dow, Kansas City, Mo.); and AMOXICILLAN™ (penicillin). The patient history included abnormal blood chemistry and osteoporosis. Family history included cerebrovascular disease in mother and grandparent and cardiovascular disease in a grandparent.

Ileum mRNA was extracted from the tissue and purified essentially as described for the HEARNOT 01 library. The mRNA was handled according to the recommended protocols in the SuperScript Plasmid System for cDNA Synthesis and Plasmid Cloning (Cat. No. 18248-013, Gibco/BRL).

The commercial plasmid pSPORT1™ (Gibco/BRL) was digested with EcoR I restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, E. coli strain JM 109. An intermediate plasmid produced by the bacteria failed to digest with EcoR I confirming the desired loss of the EcoR I restriction site.

This intermediate plasmid (pSPORT1-ΔRI) was then digested with Hind III restriction enzyme (New England Biolabs) and the overhang was filled in with Kienow and dNTPs. A 10-mer Eco RI linker was phosphorylated and ligated onto the blunt ends. The product of the ligation reaction was digested with EcoR I and self-ligated. Following transformation into JM 109 host cells, plasmids were isolated and screened for the digestibility with EcoR I but not with Hind III. A single colony which met this criteria was designated pINCY 1. The plasmid produced by this colony was sequenced and found to contain several copies of the 10-mer linker. These extra linkers did not present a problem as they were eliminated when the vector was prepared for cloning.

The plasmid was tested for its ability to incorporate cDNAs from a library prepared using Not I and EcoR I restriction enzymes. Several clones were sequenced and a single clone containing an insert of approximately 0.8 kb was selected to prepare a large quantity of the plasmid for library production. After digestion with Not I and EcoR I, the plasmid and the cDNA insert were isolated on an agarose gel and the vector was purified on a QIAQUICK™, silica-gel purification (Qiagen, Inc.) column for use in library construction.

cDNAs were fractionated on a SEPHAROSE CLB4™, size exclusion gel chromatography column (Cat. No. 275105-01, Pharmacia Upjohn), and those cDNAs exceeding 400 bp were ligated into pSport I. The plasmid pSport I was subsequently transformed into DH5α™ competent cells (Cat. No.18258-012, Gibco/BRL).

II Isolation and Sequencing of cDNA Clones

Plasmid or phagemid DNA was released from cells and purified using MINIPREP™, a plasmid purification kit (Cat. No. 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. No. 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R at 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPSTM™ DNA Purification System (Cat. No. A7100, Promega) or QIAWELL™-8 Plasmid, QIAWELL PLUS DNA™ and QIAWELL ULTRA DNA™ Purification Systems (Qiagen, Inc.).

The cDNAs were sequenced by the method of Sanger F. and A. R. Coulson (1975; J. Mol. Biol. 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HLIM occurs. Abundance and percent abundance are also reported. Abundance directly reflects the number of times a particular transcript is represented in a cDNA library, and percent abundance is abundance divided by the total number of sequences examined in the cDNA library.

V Extension of HLIM-Encoding Polynucleotides to Full Length or to Recover Regulatory Sequences Full length HLIM-encoding nucleic acid sequence (SEQ ID NO:2, SEQ ID NO:4, or SEQ ID NO:6) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR™, a PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK™, DNA agarose gel isolation kit (Qiagen Inc.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [γ$^{32}$P] adenosine triphosphate (Amersham) and T4 polynucleotide kinase (DuPont NEN®, Boston, Mass.). The labeled oligonucleotides are substantially purified with a SEPHADEX™ G-25 size exclusion agarose bead superfine resin column (Pharrnacia & Upjohn). A portion containing 10$^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the HLIM-encoding sequence, or any part thereof, is used to inhibit in vivo or in vitro expression of naturally occurring HLIM. Although use of antisense oligonucleotides, comprising about 20 base-pairs, is specifically described, essentially the same procedure is used with larger cDNA fragments. An oligonucleotide based on the coding sequences of HLIM, as shown in FIGS. 1, 2, and 3, is used to inhibit expression of naturally occurring HLIM. The complementary oligonucleotide is designed from the most unique 5' sequence as shown in FIGS. 1, 2, and 3 and used either to inhibit transcription by preventing promoter binding to the upstream nontranslated sequence or translation of an HLIM-encoding transcript by preventing the ribosome from binding. Using an appropriate portion of the signal and 5' sequence of SEQ ID NO:2, SEQ ID NO:4, or SEQ ID NO:6, an effective antisense oligonucleotide includes any 15–20 nucleotides spanning the region which translates into the signal or 5' coding sequence of the polypeptide as shown in FIGS. 1, 2, and 3.

VIII Expression of HLIM

Expression of HLIM is accomplished by subcloning the cDNAs into appropriate vectors and transforming the vectors into host cells. In this case, the cloning vector, pSport, previously used for the generation of the cDNA library is used to express HLIM in E. coli.

Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HLIM into the bacterial growth media which can be used directly in the following assay for activity.

IX Demonstration of HLIM Activity

The binding of Zn$^{2+}$ to HLIM is assayed by monitoring the resulting changes in enthalpy (heat production or absorption) in an isothermal titration microcalorimeter (Micro-Cal Inc., Northampton, Mass.). Titration microcalorimetry measurements do not require labeling of the ligand or receptor molecules; detection is based solely on the intrinsic change in the heat of enthalpy upon binding. Multiple computer-controlled injections of a known volume of ZnCl$_2$ solution are directed into a thermally-controlled chamber containing HLIM. The change in enthalpy after each injection is plotted against the number of injections, producing a binding isotherm. The volumes and concentrations of the injected ZnCl$_2$ solution and of the HLIM solution are used along with the binding isotherm to calculate values for the number, affinity, and association constant of HLIM with the Zn$^{2+}$ ligand.

X Production of HLIM Specific Antibodies

HLIM that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR™ software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HLIM Using Specific Antibodies

Naturally occurring or recombinant HLIM is substantially purified by immunoaffinity chromatography using antibodies specific for HLIM. An immunoaffinity column is constructed by covalently coupling HLIM antibody to an activated chromatographic resin, such as CnBr-activated SEPHAROSE™, size exclusion gel chromatography agarose beads (Pharmacia & Upjohn). After the coupling, the resin is blocked and washed according to the manufacturer's instructions.

Media containing HLIM is passed over the immunoaffinity column, and the column is washed under conditions that allow the preferential absorbance of HLIM (e.g., high ionic strength buffers in the presence of detergent). The column is eluted under conditions that disrupt antibody/HLIM binding (eg, a buffer of pH 2–3 or a high concentration of a chaotrope, such as urea or thiocyanate ion), and HLIM is collected.

XII Identification of Molecules Which Interact with HLIM

HLIM or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HLIM, washed and any wells with labeled HLIM complex are assayed. Data obtained using different concentrations of HLIM are used to calculate values for the number, affinity, and association of HLIM with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polypeptide consisting of the amino acid sequence of SEQ ID NO:1.

2. A composition comprising an isolated and purified polypeptide consisting of the amino acid sequence of SEQ ID NO:1 in conjunction with a suitable carrier.

* * * * *

UNITED STATES PATENT AND TRADEMARK OFFICE
CERTIFICATE OF CORRECTION

PATENT NO. : 5,863,898
DATED : January 26, 1999
INVENTOR(S) : Goli et al.

Page 1 of 1

It is certified that error appears in the above-identified patent and that said Letters Patent is hereby corrected as shown below:

Title Page,
Delete "[22] Filed: Oct. 28, 1996" and insert --[22] Filed: Oct. 29, 1996--.

Signed and Sealed this

Twenty-sixth Day of June, 2001

Attest:

Attesting Officer

NICHOLAS P. GODICI
Acting Director of the United States Patent and Trademark Office

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:1:

```
Met Pro Val Trp Gly Gly Gly Asn Lys Cys Gly Ala Cys Gly Arg Thr
  1               5                  10                  15
Val Tyr His Ala Glu Glu Val Gln Cys Asp Gly Arg Ser Phe His Arg
             20                  25                  30
Cys Cys Phe Leu Cys Met Val Cys Arg Lys Asn Leu Asp Ser Thr Thr
         35                  40                  45
Val Ala Ile His Asp Glu Glu Ile Tyr Cys Lys Ser Cys Tyr Gly Lys
     50                  55                  60
Lys Tyr Gly Pro Lys Gly Tyr Gly Tyr Gly Gln Gly Ala Gly Thr Leu
 65                  70                  75                  80
Xaa Met Asp Arg Gly Glu Arg Leu Gly Ile Lys Pro Glu Ser Val Gln
                 85                  90                  95
Pro His Arg Pro Thr Thr Asn Pro Asn Xaa Ser Lys Phe Ala Gln Lys
                100                 105                 110
Tyr Gly Gly Ala Glu Lys Cys Ser Arg Cys Gly Asp Ser Val Tyr Ala
            115                 120                 125
Ala Glu Lys Ile Ile Gly Ala Gly Lys Pro Trp His Lys Asn Cys Phe
        130                 135                 140
Arg Cys Ala Lys Cys Gly Lys Ser Leu Glu Ser Thr Thr Leu Thr Glu
145                 150                 155                 160
Lys Glu Gly Glu Ile Tyr Cys Lys Gly Cys Tyr Ala Lys Asn Phe Gly
                165                 170                 175
Pro Lys Gly Phe Gly Phe Gly Gln Gly Ala Gly Ala Leu Val His Ser
            180                 185                 190
Glu
```

( 2 ) INFORMATION FOR SEQ ID NO:2:

( i ) SEQUENCE CHARACTERISTICS:
        ( A ) LENGTH: 797 base pairs
        ( B ) TYPE: nucleic acid (C) STRANDEDNESS: single
(D) TOPOLOGY: linear (vii) IMMEDIATE SOURCE:
(A) LIBRARY: Consensus
(B) CLONE: Consensus (xi) SEQUENCE DESCRIPTION: SEQ ID NO:2:

| | | | | | |
|---|---|---|---|---|---|
| CTGGACCCTC | CCTCCAGCCC | AGCCTCGCTA | GCTCCGCCTG | CGGTACGTGC | TCCCGCCTCC | 60 |
| GACTCAAAAT | GCCTGTCTGG | GGAGGTGGAA | ACAAGTGTGG | GGCCTGTGGG | AGGACCGTGT | 120 |
| ACCACGCAGA | AGAGGTGCAG | TGTGATGGCA | GGAGCTTCCA | CCGCTGCTGC | TTTCTCTGCA | 180 |
| TGGTTTGCAG | GAAAAATTTA | GATAGCACAA | CAGTGGCAAT | TCACGATGAA | GAGATCTACT | 240 |
| GCAAATCCTG | CTACGGAAAG | AAGTATGGGC | CAAAAGGCTA | CGGTTATGGC | CAGGGCGCTG | 300 |
| GCACGCTTAA | MATGGACCGT | GGCGAGAGGC | TTGGCATCAA | ACCAGAGAGT | GTTCAGCCTC | 360 |
| ACAGGCCTAC | AACAAATCCA | AACAHTTCTA | AATTTGCTCA | GAAATATGGA | GGTGCTGAGA | 420 |
| AGTGTTCCAG | ATGTGGGGAT | TCTGTATATG | CTGCCGAGAA | GATAATTGGA | GCTGGAAAGC | 480 |
| CCTGGCACAA | AAACTGTTTC | CGATGTGCAA | AGTGTGGGAA | GAGTCTTGAA | TCAACAACTC | 540 |
| TGACTGAAAA | AGAAGGTGAG | ATTTACTGCA | AAGGATGTTA | TGCTAAAAAC | TTCGGGCCCA | 600 |
| AGGGCTTTGG | TTTTGGGCAA | GGAGCTGGGG | CCTTGGTCCA | CTCTGAGTGA | GGCCACCATC | 660 |
| ACCCACCACA | CCCTGCCCAC | TCCTGCGCTT | TTCATCGCCA | TTCCATTCCC | AGCAGCTTTG | 720 |
| GAGACCTCCA | GGATTATTTC | TCTGTCAGCC | CTGCCACATA | TCACTAATGA | CTTGAACTTG | 780 |
| GGCATCTGGC | TCCCTTT | | | | | 797 |

(2) INFORMATION FOR SEQ ID NO:3:

(i) SEQUENCE CHARACTERISTICS:
(A) LENGTH: 329 amino acids
(B) TYPE: amino acid
(C) STRANDEDNESS: single
(D) TOPOLOGY: linear (vii) IMMEDIATE SOURCE:
(A) LIBRARY: Consensus
(B) CLONE: Consensus (xi) SEQUENCE DESCRIPTION: SEQ ID NO:3:

| Met | Thr | Thr | Gln | Gln | Ile | Asp | Leu | Gln | Gly | Pro | Gly | Pro | Trp | Gly | Phe |
|---|---|---|---|---|---|---|---|---|---|---|---|---|---|---|---|
| 1 | | | | 5 | | | | | 10 | | | | | 15 | |

| Arg | Leu | Val | Gly | Gly | Lys | Asp | Phe | Glu | Gln | Pro | Leu | Ala | Ile | Ser | Arg |
|---|---|---|---|---|---|---|---|---|---|---|---|---|---|---|---|
| | | | | 20 | | | | 25 | | | | | 30 | | |

| Val | Thr | Pro | Gly | Ser | Lys | Ala | Ala | Leu | Ala | Asn | Leu | Cys | Ile | Gly | Asp |
|---|---|---|---|---|---|---|---|---|---|---|---|---|---|---|---|
| | | 35 | | | | | 40 | | | | | 45 | | | |

| Val | Ile | Thr | Ala | Ile | Asp | Gly | Glu | Asn | Thr | Ser | Asn | Met | Thr | His | Leu |
|---|---|---|---|---|---|---|---|---|---|---|---|---|---|---|---|
| | 50 | | | | | 55 | | | | | 60 | | | | |

| Glu | Ala | Gln | Asn | Arg | Ile | Lys | Gly | Cys | Thr | Asp | Asn | Leu | Thr | Leu | Thr |
|---|---|---|---|---|---|---|---|---|---|---|---|---|---|---|---|
| 65 | | | | | 70 | | | | 75 | | | | | 80 | |

| Val | Ala | Arg | Ser | Glu | His | Lys | Val | Trp | Ser | Pro | Leu | Val | Thr | Glu | Glu |
|---|---|---|---|---|---|---|---|---|---|---|---|---|---|---|---|
| | | | | 85 | | | | 90 | | | | | 95 | | |

| Gly | Lys | Arg | His | Pro | Tyr | Lys | Met | Asn | Leu | Ala | Ser | Glu | Pro | Gln | Glu |
|---|---|---|---|---|---|---|---|---|---|---|---|---|---|---|---|
| | | | 100 | | | | | 105 | | | | | 110 | | |

| Val | Leu | His | Ile | Gly | Ser | Ala | His | Asn | Arg | Ser | Ala | Met | Pro | Phe | Thr |
|---|---|---|---|---|---|---|---|---|---|---|---|---|---|---|---|
| | | 115 | | | | | 120 | | | | | 125 | | | |

| Ala | Ser | Pro | Ala | Ser | Ser | Thr | Thr | Ala | Arg | Val | Ile | Thr | Asn | Gln | Tyr |
|---|---|---|---|---|---|---|---|---|---|---|---|---|---|---|---|
| | 130 | | | | | 135 | | | | | 140 | | | | |

| Asn | Asn | Pro | Ala | Gly | Leu | Tyr | Ser | Ser | Glu | Asn | Ile | Ser | Asn | Phe | Asn |

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Asn | Ala | Leu | Glu | Ser | Lys | Thr | Ala | Ala | Ser | Gly | Val | Glu | Ala | Asn | Ser |
|     |     |     |     | 165 |     |     |     |     | 170 |     |     |     |     | 175 |     |
| Arg | Pro | Leu | Asp | His | Ala | Gln | Pro | Pro | Ser | Ser | Leu | Val | Ile | Asp | Lys |
|     |     |     | 180 |     |     |     |     | 185 |     |     |     |     | 190 |     |     |
| Glu | Ser | Glu | Val | Tyr | Lys | Met | Leu | Gln | Glu | Lys | Gln | Glu | Leu | Asn | Glu |
|     |     | 195 |     |     |     |     | 200 |     |     |     |     | 205 |     |     |     |
| Pro | Pro | Lys | Gln | Ser | Thr | Ser | Phe | Leu | Val | Leu | Gln | Glu | Ile | Leu | Glu |
|     | 210 |     |     |     |     | 215 |     |     |     |     | 220 |     |     |     |     |
| Ser | Glu | Glu | Lys | Gly | Asp | Pro | Asn | Lys | Pro | Ser | Gly | Phe | Arg | Ser | Val |
| 225 |     |     |     |     | 230 |     |     |     |     | 235 |     |     |     |     | 240 |
| Lys | Ala | Pro | Val | Thr | Lys | Val | Ala | Ala | Ser | Ile | Gly | Asn | Ala | Gln | Lys |
|     |     |     |     | 245 |     |     |     |     | 250 |     |     |     |     | 255 |     |
| Leu | Pro | Met | Cys | Asp | Lys | Cys | Gly | Thr | Gly | Ile | Val | Gly | Val | Phe | Val |
|     |     |     | 260 |     |     |     |     | 265 |     |     |     |     | 270 |     |     |
| Lys | Leu | Arg | Asp | Arg | His | Arg | His | Pro | Glu | Cys | Tyr | Val | Cys | Thr | Asp |
|     |     | 275 |     |     |     |     | 280 |     |     |     |     | 285 |     |     |     |
| Cys | Gly | Thr | Asn | Leu | Lys | Gln | Lys | Gly | His | Phe | Phe | Val | Glu | Asp | Gln |
|     | 290 |     |     |     |     | 295 |     |     |     |     | 300 |     |     |     |     |
| Ile | Tyr | Cys | Glu | Lys | His | Ala | Arg | Glu | Arg | Val | Thr | Pro | Pro | Glu | Gly |
| 305 |     |     |     |     | 310 |     |     |     |     | 315 |     |     |     |     | 320 |
| Tyr | Glu | Val | Val | Thr | Val | Phe | Pro | Lys |
|     |     |     |     | 325 |     |     |     |     |

( 2 ) INFORMATION FOR SEQ ID NO:4:

( i ) SEQUENCE CHARACTERISTICS:
        ( A ) LENGTH: 1225 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:4:

| | | | | | |
|---|---|---|---|---|---|
| GGCCCNNGCC | GCGCCGCTNT | NTCTCCNACA | NGCCGCCGGG | GGTGCCCTGC | AAGCTGTTCC | 60 |
| GCGCGTCCTG | CCCGTCTGTC | CCCGCGGGTC | GTCGCCCGCC | ACAGCCGCGC | CATGACCACC | 120 |
| CAGCAGATAG | ACCTCCAGGG | CCCGGGGCCG | TGGGGCTTCC | GCCTCGTGGG | CGGCAAGGAC | 180 |
| TTCGAGCAGC | CTCTCGCCAT | TTCCCGGGTC | ACTCCTGGAA | GCAAGGCGGC | TCTAGCTAAT | 240 |
| TTATGTATTG | GAGATGTAAT | CACAGCCATT | GATGGGGAAA | ATACTAGCAA | TATGACACAC | 300 |
| TTGGAAGCTC | AGAACAGAAT | CAAAGGCTGC | ACAGACAACT | TGACTCTCAC | TGTAGCCAGA | 360 |
| TCTGAACATA | AAGTCTGGTC | TCCTCTGGTG | ACGGAGGAAG | GGAAGCGTCA | TCCATACAAG | 420 |
| ATGAATTTAG | CCTCTGAACC | CCAGGAGGTC | CTGCACATAG | GAAGCGCCCA | CAACCGAAGT | 480 |
| GCCATGCCCT | TTACCGCCTC | GCCTGCCTCC | AGCACTACTG | CCAGGGTCAT | CACAAACCAG | 540 |
| TACAACAACC | CAGCTGGCCT | CTACTCTTCT | GAAAATATCT | CCAACTTCAA | CAATGCCCTG | 600 |
| GAGTCAAAGA | CTGCTGCCAG | CGGGGTGGAG | GCGAACAGCA | GACCCTTAGA | CCATGCTCAG | 660 |
| CCTCCAAGCA | GCCTTGTCAT | CGACAAAGAA | TCTGAAGTTT | ACAAGATGCT | TCAGGAGAAA | 720 |
| CAGGAGTTGA | ATGAGCCCCC | GAAACAGTCC | ACGTCTTTCT | TGGTTTTGCA | GGAAATCCTG | 780 |
| GAGTCTGAAG | AAAAAGGGGA | TCCCAACAAG | CCCTCAGGAT | TCAGAAGTGT | TAAAGCTCCT | 840 |
| GTCACTAAAG | TGGCTGCGTC | GATTGGAAAT | GCTCAGAAGT | TGCCTATGTG | TGACAAATGT | 900 |

```
GGCACTGGGA    TTGTTGGTGT    GTTTGTGAAG    CTGCGGGACC    GTCACCGCCA    CCCTGAGTGT         960

TATGTGTGCA    CTGACTGTGG    CACCAACCTG    AAACAGAAGG    GCCATTTCTT    TGTGGAGGAT        1020

CAAATCTACT    GTGAGAAGCA    TGCCCGGGAG    CGAGTCACAC    CACCTGAGGG    TTATGAAGTG        1080

GTCACTGTGT    TCCCCAAGTG    AGCCAGCAGA    TCYGACCACT    GTTCTCCAGC    AGGCCTCTGC        1140

TGCAGCTTTT    TCTCTCAGTG    TTCTGGCCCT    CTCCTCTCTT    GAAAGTTCTC    TGCCTACTTT        1200

GGTTTTCCCT    CTGCTTGTAA    AACAT                                                      1225
```

( 2 ) INFORMATION FOR SEQ ID NO:5:

( i ) SEQUENCE CHARACTERISTICS:
        ( A ) LENGTH: 316 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:5:

```
Met  Pro  Gln  Thr  Val  Ile  Leu  Pro  Gly  Pro  Ala  Pro  Trp  Gly  Phe  Arg
 1                   5                    10                      15

Leu  Ser  Gly  Gly  Ile  Asp  Phe  Asn  Gln  Pro  Leu  Val  Ile  Thr  Arg  Ile
              20                         25                       30

Thr  Pro  Gly  Ser  Lys  Ala  Ala  Ala  Asn  Leu  Cys  Pro  Gly  Asp  Val
              35                    40                   45

Ile  Leu  Ala  Ile  Asp  Gly  Phe  Gly  Thr  Glu  Ser  Met  Thr  His  Ala  Asp
         50                    55                    60

Ala  Gln  Asp  Arg  Ile  Lys  Ala  Ala  Ala  His  Gln  Leu  Cys  Leu  Lys  Ile
 65                       70                         75                      80

Asp  Arg  Gly  Glu  Thr  His  Leu  Trp  Ser  Pro  Gln  Val  Ser  Glu  Asp  Gly
                   85                         90                        95

Lys  Ala  His  Pro  Phe  Lys  Ile  Asn  Leu  Glu  Ser  Glu  Pro  Gln  Glu  Phe
                  100                        105                      110

Lys  Pro  Ile  Gly  Thr  Ala  His  Asn  Arg  Arg  Ala  Gln  Pro  Phe  Val  Ala
              115                      120                      125

Ala  Ala  Asn  Ile  Asp  Asp  Lys  Arg  Gln  Val  Val  Ser  Ala  Ser  Tyr  Asn
    130                       135                       140

Ser  Pro  Ile  Gly  Leu  Tyr  Ser  Thr  Ser  Asn  Ile  Gln  Asp  Ala  Leu  His
145                      150                      155                      160

Gly  Gln  Leu  Arg  Gly  Leu  Ile  Pro  Ser  Ser  Pro  Gln  Asn  Glu  Pro  Thr
                   165                       170                      175

Ala  Ser  Val  Pro  Pro  Glu  Ser  Asp  Val  Tyr  Arg  Met  Leu  His  Asp  Asn
              180                       185                      190

Arg  Asn  Glu  Pro  Thr  Gln  Pro  Arg  Gln  Ser  Gly  Ser  Phe  Arg  Val  Leu
              195                      200                      205

Gln  Gly  Met  Val  Asp  Asp  Gly  Phe  Asp  Asp  Arg  Pro  Ala  Gly  Thr  Arg
    210                       215                      220

Ser  Val  Arg  Ala  Pro  Val  Thr  Lys  Val  His  Gly  Gly  Ser  Gly  Gly  Ala
225                       230                      235                      240

Gln  Arg  Met  Pro  Val  Cys  Asp  Lys  Cys  Gly  Ser  Gly  Ile  Val  Gly  Ala
                   245                      250                      255

Val  Val  Lys  Ala  Arg  Asp  Lys  Tyr  Arg  His  Pro  Glu  Cys  Phe  Val  Cys
              260                      265                      270

Ala  Asp  Cys  Asn  Leu  Asn  Leu  Lys  Gln  Lys  Gly  Tyr  Phe  Phe  Ile  Glu
              275                      280                      285
```

```
Gly Glu Leu Tyr Cys Glu Thr His Ala Arg Ala Arg Thr Lys Pro Pro
        290                 295                 300

Glu Gly Tyr Asp Thr Val Thr Leu Tyr Pro Lys Ala
305                     310                 315
```

( 2 ) INFORMATION FOR SEQ ID NO:6:

( i ) SEQUENCE CHARACTERISTICS:
        ( A ) LENGTH: 1336 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: Consensus
        ( B ) CLONE: Consensus ( x i ) SEQUENCE DESCRIPTION: SEQ ID NO:6:

```
CGGCTCGAGC  GGCTCGAGGG  CGCGGAGTGG  CTGCCCTGCG  CGGGGACACT  CAGAGCCCGG    60
TGGGCGGGAG  GAAGGCGGCA  TGCCCCAGAC  GGTGATCCTC  CCGGGCCCTG  CGCCCTGGGG   120
CTTCAGGCTC  TCAGGGGGCA  TAGACTTCAA  CCAGCCTTTG  GTCATCACCA  GGATTACACC   180
AGGAAGCAAG  GCGGCAGCTG  CCAACCTGTG  TCCTGGAGAT  GTCATCCTGG  CTATTGACGG   240
CTTTGGGACA  GAGTCCATGA  CTCATGCTGA  TGCGCAGGAC  AGGATTAAAG  CAGCAGCTCA   300
CCAGCTGTGT  CTCAAAATTG  ACAGGGGAGA  AACTCACTTA  TGGTCTCCAC  AAGTATCTGA   360
AGATGGGAAA  GCCCATCCTT  TCAAAATCAA  CTTAGAATCA  GAACCACAGG  AATTCAAACC   420
CATTGGTACC  GCGCACAACA  GAAGGGCCCA  GCCTTTTGTT  GCAGCTGCAA  ACATTGATGA   480
CAAAAGACAG  GTAGTGAGCG  CTTCCTATAA  CTCGCCAATT  GGGCTCTATT  CAACTAGCAA   540
TATACAAGAT  GCGCTTCACG  GACAGCTGCG  GGGTCTCATT  CCTAGCTCAC  CTCAAAACGA   600
GCCCACAGCC  TCGGTGCCCC  CCGAGTCGGA  CGTGTACCGG  ATGCTCCACG  ACAATCGGAA   660
TGAGCCCACA  CAGCCTCGCC  AGTCGGGCTC  CTTCAGAGTG  CTCCAGGGAA  TGGTGGACGA   720
TGGGTTTGAT  GACCGTCCGG  CTGGAACGCG  GAGTGTGAGA  GCTCCGGTGA  CGAAAGTCCA   780
TGGCGGTTCA  GGCGGGGCAC  AGAGGATGCC  GGTCTGTGAC  AAATGTGGGA  GTGGCATAGT   840
TGGTGCTGTG  GTGAAGGCGC  GGGATAAGTA  CCGGCACCCT  GAGTGCTTCG  TGTGTGCCGA   900
CTGCAACCTC  AACCTCAAGC  AAAAGGGCTA  CTTCTTCATA  GAAGGGGAGC  TGTACTGCGA   960
AACCCACGCA  AGAGCCCGCA  CAAAGCCCCC  AGAGGGCTAT  GACACGGTCA  CTCTGTATCC  1020
CAAAGCTTAA  GTCTCTGCAG  GCGTGGCACG  CACGCACGCA  CCCACCCACG  CGCCACTTAC  1080
ACGAGAAGAC  ATTCATGGCT  TTGGGCAGAA  GGATTGTGCA  GATTGTCAAC  TCCAAATCTA  1140
AAGTCAAGGC  TTTAGACCTT  TATCCTATTG  TTTATTGAGG  AAAAGGAATG  GGAGGCAAAT  1200
GCCTGCTATG  TGAAAAAAAC  ATACACTTAG  CTATGTTTTG  CAACTCTTTT  TGGGGCTAGC  1260
AATAATGATA  TTTAAAGCAA  TAATTTTTTG  TATGTCATAC  TCCACAATTT  ACATGTATAT  1320
TACAGCCATC  AAACAC                                                     1336
```

( 2 ) INFORMATION FOR SEQ ID NO:7:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 118161

( x i ) SEQUENCE DESCRIPTION: SEQ ID NO:7:

| Met | Pro | Asn | Trp | Gly | Gly | Gly | Lys | Lys | Cys | Gly | Val | Cys | Gln | Lys | Thr |
| 1 | | | | 5 | | | | | 10 | | | | | 15 | |

| Val | Tyr | Phe | Ala | Glu | Glu | Val | Gln | Cys | Glu | Gly | Asn | Ser | Phe | His | Lys |
| | | | 20 | | | | | 25 | | | | | 30 | | |

| Ser | Cys | Phe | Leu | Cys | Met | Val | Cys | Lys | Lys | Asn | Leu | Asp | Ser | Thr | Thr |
| | | | 35 | | | | 40 | | | | | 45 | | | |

| Val | Ala | Val | His | Gly | Glu | Glu | Ile | Tyr | Cys | Lys | Ser | Cys | Tyr | Gly | Lys |
| | | 50 | | | | 55 | | | | | 60 | | | | |

| Lys | Tyr | Gly | Pro | Lys | Gly | Tyr | Gly | Tyr | Gly | Gln | Gly | Ala | Gly | Thr | Leu |
| 65 | | | | | 70 | | | | | 75 | | | | | 80 |

| Ser | Thr | Asp | Lys | Gly | Glu | Ser | Leu | Gly | Ile | Lys | His | Glu | Glu | Ala | Pro |
| | | | | 85 | | | | | 90 | | | | | 95 | |

| Gly | His | Arg | Pro | Thr | Thr | Asn | Pro | Asn | Ala | Ser | Lys | Phe | Ala | Gln | Lys |
| | | | 100 | | | | | 105 | | | | | 110 | | |

| Ile | Gly | Gly | Ser | Glu | Arg | Cys | Pro | Arg | Cys | Ser | Gln | Ala | Val | Tyr | Ala |
| | | 115 | | | | | 120 | | | | | 125 | | | |

| Ala | Glu | Lys | Val | Ile | Gly | Ala | Gly | Lys | Ser | Trp | His | Lys | Ala | Cys | Phe |
| | 130 | | | | | 135 | | | | | 140 | | | | |

| Arg | Cys | Ala | Lys | Cys | Gly | Lys | Gly | Leu | Glu | Ser | Thr | Thr | Leu | Ala | Asp |
| 145 | | | | | 150 | | | | | 155 | | | | | 160 |

| Lys | Asp | Gly | Glu | Ile | Tyr | Cys | Lys | Gly | Cys | Tyr | Ala | Lys | Asn | Phe | Gly |
| | | | | 165 | | | | | 170 | | | | | 175 | |

| Pro | Lys | Gly | Phe | Gly | Phe | Gly | Gln | Gly | Ala | Gly | Ala | Leu | Val | His | Ser |
| | | | 180 | | | | | 185 | | | | | 190 | | |

Glu ( 2 ) INFORMATION FOR SEQ ID NO:8:

( i ) SEQUENCE CHARACTERISTICS:
        ( A ) LENGTH: 194 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1234841

( x i ) SEQUENCE DESCRIPTION: SEQ ID NO:8:

| Met | Pro | Asn | Trp | Gly | Gly | Gly | Ala | Lys | Cys | Gly | Ala | Cys | Glu | Lys | Thr |
| 1 | | | | 5 | | | | | 10 | | | | | 15 | |

| Val | Tyr | His | Ala | Glu | Glu | Ile | Gln | Cys | Asn | Gly | Arg | Ser | Phe | His | Lys |
| | | | 20 | | | | | 25 | | | | | 30 | | |

| Thr | Cys | Phe | His | Cys | Met | Ala | Cys | Arg | Lys | Ala | Leu | Asp | Ser | Thr | Thr |
| | | | 35 | | | | 40 | | | | | 45 | | | |

| Val | Ala | Ala | His | Glu | Ser | Glu | Ile | Tyr | Cys | Lys | Val | Cys | Tyr | Gly | Arg |
| | | 50 | | | | 55 | | | | | 60 | | | | |

| Arg | Tyr | Gly | Pro | Lys | Gly | Ile | Gly | Tyr | Gly | Gln | Gly | Ala | Gly | Cys | Leu |
| 65 | | | | | 70 | | | | | 75 | | | | | 80 |

| Ser | Thr | Asp | Thr | Gly | Glu | His | Leu | Gly | Leu | Gln | Phe | Gln | Gln | Ser | Pro |
| | | | | 85 | | | | | 90 | | | | | 95 | |

| Lys | Pro | Ala | Arg | Ser | Val | Thr | Thr | Ser | Asn | Pro | Ser | Lys | Phe | Thr | Ala |
| | | | 100 | | | | | 105 | | | | | 110 | | |

| Lys | Phe | Gly | Glu | Ser | Glu | Lys | Cys | Pro | Arg | Cys | Gly | Lys | Ser | Val | Tyr |
| | | 115 | | | | | 120 | | | | | 125 | | | |

```
Ala  Ala  Glu  Lys  Val  Met  Gly  Gly  Lys  Pro  Trp  His  Lys  Thr  Cys
     130                      135                140

Phe  Arg  Cys  Ala  Ile  Cys  Gly  Lys  Ser  Leu  Glu  Ser  Thr  Asn  Val  Thr
145                      150                     155                          160

Asp  Lys  Asp  Gly  Glu  Leu  Tyr  Cys  Lys  Val  Cys  Tyr  Ala  Lys  Asn  Phe
               165                     170                          175

Gly  Pro  Thr  Gly  Ile  Gly  Phe  Gly  Gly  Leu  Thr  Gln  Gln  Val  Glu  Lys
               180                     185                          190

Lys  Glu
```

(2) INFORMATION FOR SEQ ID NO:9:

(i) SEQUENCE CHARACTERISTICS:
        (A) LENGTH: 193 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1314351

(xi) SEQUENCE DESCRIPTION: SEQ ID NO:9:

```
Met  Pro  Val  Trp  Gly  Gly  Gly  Asn  Lys  Cys  Gly  Ala  Cys  Gly  Arg  Thr
1                        5                     10                          15

Val  Tyr  His  Ala  Glu  Glu  Val  Gln  Cys  Asp  Gly  Arg  Thr  Phe  His  Arg
               20                     25                          30

Cys  Cys  Phe  Leu  Cys  Met  Val  Cys  Arg  Lys  Asn  Leu  Asp  Ser  Thr  Thr
               35                     40                          45

Val  Ala  Ile  His  Asp  Glu  Glu  Ile  Tyr  Cys  Lys  Ser  Cys  Tyr  Gly  Lys
     50                      55                     60

Lys  Tyr  Gly  Pro  Lys  Gly  Tyr  Gly  Tyr  Gly  Gln  Gly  Ala  Gly  Thr  Leu
65                       70                     75                          80

Asn  Met  Asp  Arg  Gly  Glu  Arg  Leu  Gly  Ile  Lys  Pro  Glu  Ser  Ala  Gln
               85                     90                          95

Pro  His  Arg  Pro  Thr  Thr  Asn  Pro  Asn  Thr  Ser  Lys  Phe  Ala  Gln  Lys
               100                    105                         110

Tyr  Gly  Gly  Ala  Glu  Lys  Cys  Ser  Arg  Cys  Gly  Asp  Ser  Val  Tyr  Ala
          115                     120                         125

Ala  Glu  Lys  Ile  Ile  Gly  Ala  Gly  Lys  Pro  Trp  His  Lys  Asn  Cys  Phe
     130                     135                     140

Arg  Cys  Ala  Lys  Cys  Gly  Lys  Ser  Leu  Glu  Ser  Thr  Thr  Leu  Thr  Glu
145                      150                     155                          160

Lys  Glu  Gly  Glu  Ile  Tyr  Cys  Lys  Gly  Cys  Tyr  Ala  Lys  Asn  Phe  Gly
               165                    170                         175

Pro  Lys  Gly  Phe  Gly  Tyr  Gly  Gln  Gly  Ala  Gly  Ala  Leu  Val  His  Ala
               180                    185                         190

Gln
```

(2) INFORMATION FOR SEQ ID NO:10:

(i) SEQUENCE CHARACTERISTICS:
        (A) LENGTH: 327 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1020151

(xi) SEQUENCE DESCRIPTION: SEQ ID NO:10:

| Met | Thr | Thr | Gln | Gln | Ile | Val | Leu | Gln | Gly | Pro | Gly | Pro | Trp | Gly | Phe |
|---|---|---|---|---|---|---|---|---|---|---|---|---|---|---|---|
| 1 | | | | 5 | | | | | 10 | | | | | 15 | |

| Arg | Leu | Val | Gly | Gly | Lys | Asp | Phe | Glu | Gln | Pro | Leu | Ala | Ile | Ser | Arg |
|---|---|---|---|---|---|---|---|---|---|---|---|---|---|---|---|
| | | | 20 | | | | | 25 | | | | | 30 | | |

| Val | Thr | Pro | Gly | Ser | Lys | Ala | Ala | Ile | Ala | Asn | Leu | Cys | Ile | Gly | Asp |
|---|---|---|---|---|---|---|---|---|---|---|---|---|---|---|---|
| | | 35 | | | | | 40 | | | | | 45 | | | |

| Leu | Ile | Thr | Ala | Ile | Asp | Gly | Glu | Asp | Thr | Ser | Ser | Met | Thr | His | Leu |
|---|---|---|---|---|---|---|---|---|---|---|---|---|---|---|---|
| | 50 | | | | | 55 | | | | | 60 | | | | |

| Glu | Ala | Gln | Asn | Lys | Ile | Lys | Gly | Cys | Val | Asp | Asn | Met | Thr | Leu | Thr |
|---|---|---|---|---|---|---|---|---|---|---|---|---|---|---|---|
| 65 | | | | | 70 | | | | | 75 | | | | | 80 |

| Val | Ser | Arg | Ser | Glu | Gln | Lys | Ile | Trp | Ser | Pro | Leu | Val | Thr | Glu | Glu |
|---|---|---|---|---|---|---|---|---|---|---|---|---|---|---|---|
| | | | | 85 | | | | | 90 | | | | | 95 | |

| Gly | Lys | Arg | His | Pro | Tyr | Lys | Met | Asn | Leu | Ala | Ser | Glu | Pro | Gln | Glu |
|---|---|---|---|---|---|---|---|---|---|---|---|---|---|---|---|
| | | | 100 | | | | | 105 | | | | | 110 | | |

| Val | Leu | His | Ile | Gly | Ser | Ala | His | Asn | Arg | Ser | Ala | Met | Pro | Phe | Thr |
|---|---|---|---|---|---|---|---|---|---|---|---|---|---|---|---|
| | | 115 | | | | | 120 | | | | | 125 | | | |

| Ala | Ser | Pro | Ala | Pro | Gly | Thr | Arg | Val | Ile | Thr | Asn | Gln | Tyr | Asn | Ser |
|---|---|---|---|---|---|---|---|---|---|---|---|---|---|---|---|
| | 130 | | | | | 135 | | | | | 140 | | | | |

| Pro | Thr | Gly | Leu | Tyr | Ser | Ser | Glu | Asn | Ile | Ser | Asn | Phe | Asn | Asn | Ala |
|---|---|---|---|---|---|---|---|---|---|---|---|---|---|---|---|
| 145 | | | | | 150 | | | | | 155 | | | | | 160 |

| Val | Glu | Ser | Lys | Thr | Ser | Ala | Ser | Gly | Glu | Glu | Ala | Asn | Ser | Arg | Pro |
|---|---|---|---|---|---|---|---|---|---|---|---|---|---|---|---|
| | | | | 165 | | | | | 170 | | | | | 175 | |

| Ser | Ala | Gln | Pro | His | Pro | Ser | Gly | Gly | Leu | Ile | Ile | Asp | Lys | Glu | Ser |
|---|---|---|---|---|---|---|---|---|---|---|---|---|---|---|---|
| | | | 180 | | | | | 185 | | | | | 190 | | |

| Glu | Val | Tyr | Lys | Met | Leu | Gln | Glu | Lys | Gln | Glu | Leu | Asn | Glu | Pro | Pro |
|---|---|---|---|---|---|---|---|---|---|---|---|---|---|---|---|
| | | 195 | | | | | 200 | | | | | 205 | | | |

| Lys | Gln | Ser | Thr | Ser | Phe | Leu | Val | Leu | Gln | Glu | Ile | Leu | Glu | Ser | Asp |
|---|---|---|---|---|---|---|---|---|---|---|---|---|---|---|---|
| | 210 | | | | | 215 | | | | | 220 | | | | |

| Gly | Lys | Gly | Asp | Pro | Asn | Lys | Pro | Ser | Gly | Phe | Arg | Ser | Val | Lys | Ala |
|---|---|---|---|---|---|---|---|---|---|---|---|---|---|---|---|
| 225 | | | | | 230 | | | | | 235 | | | | | 240 |

| Pro | Val | Thr | Lys | Val | Ala | Ala | Ser | Val | Gly | Asn | Ala | Gln | Lys | Leu | Pro |
|---|---|---|---|---|---|---|---|---|---|---|---|---|---|---|---|
| | | | | 245 | | | | | 250 | | | | | 255 | |

| Ile | Cys | Asp | Lys | Cys | Gly | Thr | Gly | Ile | Val | Gly | Val | Phe | Val | Lys | Leu |
|---|---|---|---|---|---|---|---|---|---|---|---|---|---|---|---|
| | | | 260 | | | | | 265 | | | | | 270 | | |

| Arg | Asp | His | His | Pro | His | Pro | Glu | Cys | Tyr | Val | Cys | Thr | Asp | Cys | Gly |
|---|---|---|---|---|---|---|---|---|---|---|---|---|---|---|---|
| | | 275 | | | | | 280 | | | | | 285 | | | |

| Ile | Asn | Leu | Lys | Gln | Lys | Gly | His | Phe | Phe | Val | Gly | Asp | Gln | Ile | Tyr |
|---|---|---|---|---|---|---|---|---|---|---|---|---|---|---|---|
| | 290 | | | | | 295 | | | | | 300 | | | | |

| Cys | Glu | Lys | His | Ala | Arg | Glu | Arg | Val | Thr | Pro | Pro | Glu | Gly | Tyr | Asp |
|---|---|---|---|---|---|---|---|---|---|---|---|---|---|---|---|
| 305 | | | | | 310 | | | | | 315 | | | | | 320 |

| Val | Val | Thr | Val | Phe | Pro | Lys |
|---|---|---|---|---|---|---|
| | | | | 325 | | |

(2) INFORMATION FOR SEQ ID NO:11:

(i) SEQUENCE CHARACTERISTICS:
        (A) LENGTH: 330 amino acids
        (B) TYPE: amino acid
        (C) STRANDEDNESS: single
        (D) TOPOLOGY: linear (vi) ORIGINAL SOURCE:
        (E) HAPLOTYPE: GenBank (vii) IMMEDIATE SOURCE:
        (A) LIBRARY: 887580

(xi) SEQUENCE DESCRIPTION: SEQ ID NO:11:

| | | | | | | | | | | | | | | |
|---|---|---|---|---|---|---|---|---|---|---|---|---|---|---|
| Met 1 | Thr | His | Ala | Val 5 | Thr | Leu | Arg | Gly | Pro 10 | Ser | Pro | Trp | Gly | Phe 15 | Arg |
| Leu | Val | Gly | Gly 20 | Arg | Asp | Phe | Ser | Ala 25 | Pro | Leu | Thr | Ile | Ser 30 | Arg | Val |
| His | Ala | Gly 35 | Ser | Lys | Ala | Ala | Leu 40 | Ala | Ala | Leu | Cys | Pro 45 | Gly | Asp | Ser |
| Ile | Gln 50 | Ala | Ile | Asn | Gly | Glu 55 | Ser | Thr | Glu | Leu | Met 60 | Thr | His | Leu | Glu |
| Ala 65 | Gln | Asn | Arg | Ile | Lys 70 | Gly | Cys | His | Asp | His 75 | Leu | Thr | Leu | Ser | Val 80 |
| Ser | Arg | Pro | Glu | Asn 85 | Lys | Asn | Trp | Pro | Ser 90 | Ser | Pro | Asn | Asp | Lys 95 | Ala |
| Gln | Ala | His | Arg 100 | Ile | His | Ile | Asp | Pro 105 | Glu | Ala | Gln | Asp | Gly 110 | Ser | Pro |
| Ala | Thr | Ser 115 | Arg | Arg | Ser | Ser | Ile 120 | Ser | Gly | Ile | Ser | Leu 125 | Glu | Asp | Asn |
| Arg | Ser 130 | Gly | Leu | Gly | Ser | Pro 135 | Tyr | Gly | Gln | Pro | Pro 140 | Arg | Leu | Pro | Val |
| Pro 145 | His | Asn | Gly | Ser | Ser 150 | Asn | Glu | Val | Thr | Leu 155 | Pro | Ser | Gln | Met | Ser 160 |
| Ala | Leu | His | Val | Ser 165 | Pro | Pro | Pro | Ser | Ala 170 | Asp | Thr | Pro | Arg | Ile 175 | Leu |
| Pro | Arg | Asn | Arg 180 | Asp | Cys | Arg | Val | Asp 185 | Leu | Gly | Ser | Glu | Val 190 | Tyr | Arg |
| Met | Leu | Arg 195 | Glu | Pro | Ala | Glu | Pro 200 | Ala | Ala | Ser | Glu | Pro 205 | Lys | Gln | Ser |
| Gly | Ser 210 | Phe | Arg | Tyr | Leu | Gln 215 | Gly | Met | Leu | Glu | Ala 220 | Gly | Glu | Gly | Gly |
| Asp 225 | Arg | Pro | Gly | Ser | Gly 230 | Gly | Ser | Arg | Asn | Leu 235 | Lys | Pro | Ala | Ala | Ser 240 |
| Lys | Leu | Gly | Ala | Pro 245 | Leu | Ser | Gly | Leu | Gln 250 | Gly | Leu | Pro | Glu | Cys 255 | Thr |
| Arg | Cys | Gly | His 260 | Gly | Ile | Val | Gly | Thr 265 | Ile | Val | Lys | Ala | Arg 270 | Asp | Lys |
| Leu | Tyr | His 275 | Pro | Glu | Cys | Phe | Met 280 | Cys | Ser | Asp | Cys | Gly 285 | Leu | Asn | Leu |
| Lys | Gln 290 | Arg | Gly | Tyr | Phe | Phe 295 | Leu | Asp | Glu | Arg | Leu 300 | Tyr | Cys | Glu | Asn |
| His 305 | Ala | Lys | Ala | Arg | Val 310 | Lys | Pro | Pro | Glu | Gly 315 | Tyr | Asp | Val | Val | Ala 320 |
| Val | Tyr | Pro | Asn | Ala 325 | Lys | Val | Glu | Leu | Val 330 | | | | | | |